(12) United States Patent
Schriver et al.

(10) Patent No.: US 10,159,788 B2
(45) Date of Patent: Dec. 25, 2018

(54) ATTACHMENT DEVICE FOR MEDICAL FLUID CONTAINER

(71) Applicant: Bayer Medical Care Inc., Indianola, PA (US)

(72) Inventors: Ralph H. Schriver, Tarentum, PA (US); James A. Dedig, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 483 days.

(21) Appl. No.: 14/888,280

(22) PCT Filed: May 1, 2014

(86) PCT No.: PCT/US2014/036294
§ 371 (c)(1),
(2) Date: Oct. 30, 2015

(87) PCT Pub. No.: WO2014/179525
PCT Pub. Date: Nov. 6, 2014

(65) Prior Publication Data
US 2016/0074580 A1   Mar. 17, 2016

Related U.S. Application Data

(60) Provisional application No. 61/818,084, filed on May 1, 2013, provisional application No. 61/914,612, filed on Dec. 11, 2013.

(51) Int. Cl.
*A61M 5/32*   (2006.01)
*A61M 5/162*   (2006.01)
(Continued)

(52) U.S. Cl.
CPC ............ *A61M 5/162* (2013.01); *A61J 1/1481* (2015.05); *A61J 1/201* (2015.05); *A61J 1/00* (2013.01);
(Continued)

(58) Field of Classification Search
CPC .......... A61M 5/162; A61J 1/1481; A61J 1/00; A61J 1/1406; A61J 1/201; A61J 1/2055; A61J 1/2065
See application file for complete search history.

(56) References Cited

U.S. PATENT DOCUMENTS 4,201,406 A   5/1980   Dennehey et al.
4,675,020 A   6/1987   McPhee
(Continued)

FOREIGN PATENT DOCUMENTS

FR           84684 E    3/1965
WO       9633769 A1   10/1996
(Continued)

OTHER PUBLICATIONS

"Supplementary European Search Report from EP Application No. EP14792097", dated Oct. 26, 2016.
(Continued)

*Primary Examiner* — Philip R Wiest
(74) *Attorney, Agent, or Firm* — Joseph L. Kent; David Schramm; James R. Stevenson

(57) ABSTRACT

An attachment device for connecting a fluid path set to a medical container includes a body having a pointed distal end configured for puncturing a membrane of the medical container and a proximal end configured for connecting to the fluid path set. The attachment device further includes a fluid channel extending along a longitudinal axis of the body between the distal end and the proximal end. The fluid channel is configured for delivering a medical fluid between the medical container and the fluid path set. At least one deflectable retaining element projects from the body of the attachment device between the distal end and the proximal end. The at least one retaining element is configured from non-removably retaining the attachment device with the
(Continued)

medical container after the attachment device is connected to the medical container.

19 Claims, 29 Drawing Sheets

(51) Int. Cl.
  *A61J 1/20* (2006.01)
  *A61J 1/00* (2006.01)
  *A61J 1/14* (2006.01)
(52) U.S. Cl.
  CPC ............ *A61J 1/1406* (2013.01); *A61J 1/2055* (2015.05); *A61J 1/2065* (2015.05)

(56) References Cited

U.S. PATENT DOCUMENTS

| | | | |
|---|---|---|---|
| 5,279,605 A | 1/1994 | Karrasch et al. | |
| 5,542,712 A * | 8/1996 | Klinger | F16L 37/0987 285/256 |
| 6,599,273 B1 * | 7/2003 | Lopez | A61J 1/20 251/149.1 |
| 6,635,044 B2 | 10/2003 | Lopez | |
| 6,958,055 B2 | 10/2005 | Donnan et al. | |
| 7,682,345 B2 | 3/2010 | Savage | |
| 7,887,528 B2 | 2/2011 | Yandell | |
| 9,358,333 B2 | 6/2016 | Trombley, III et al. | |
| 2004/0073175 A1 | 4/2004 | Jacobson et al. | |
| 2004/0158205 A1 | 8/2004 | Savage | |
| 2005/0015074 A1 | 1/2005 | Trombley | |
| 2005/0027233 A1 | 2/2005 | Flaherty | |
| 2006/0200093 A1 | 9/2006 | Lopez | |
| 2008/0249499 A1 | 10/2008 | Vancaillie et al. | |
| 2010/0160889 A1 | 6/2010 | Smith et al. | |
| 2010/0256486 A1 | 10/2010 | Savage | |
| 2013/0053814 A1 | 2/2013 | Mueller-Beckhaus et al. | |
| 2014/0230368 A1 | 8/2014 | Trocki et al. | |

FOREIGN PATENT DOCUMENTS

| | | |
|---|---|---|
| WO | 9702853 A1 | 1/1997 |
| WO | 2011039747 A1 | 4/2011 |

OTHER PUBLICATIONS

The International Preliminary Report and Written Opinion dated Nov. 12, 2015 from corresponding PCT Application No. PCT/US2014/036294.

The International Search Report and Written Opinion dated Oct. 3, 2014 from corresponding PCT Application No. PCT/US2014/036294.

* cited by examiner

ATTACHMENT DEVICE FOR MEDICAL FLUID CONTAINER

CROSS-REFERENCE TO RELATED APPLICATIONS

This application is a U.S. national stage filing under 35 U.S.C. § 371 of International Application No. PCT/US2014/036294, filed May 1, 2014, which claims priority to U.S. Provisional Patent Application No. 61/818,084, filed on May 1, 2013 and entitled "Attachment Device for Medical Fluid Container", and U.S. Provisional Patent Application No. 61/914,612, filed on Dec. 11, 2013 and entitled "Attachment Device for Medical Fluid Container", the disclosures of which are hereby incorporated by reference in their entirety.

BACKGROUND OF THE DISCLOSURE

Field of the Disclosure

The present disclosure is directed to medical fluid delivery applications and, particularly, to an attachment device for a medical container.

Description of Related Art

In many medical diagnostic and therapeutic procedures, a medical practitioner, such as a physician, injects a patient with a medical fluid. Such a medical fluid is typically stored in a medical container, such as a vial or a bag. In general, medical containers have an outlet port adapted for connection with an attachment device, such as a spike, such that the medical fluid from the container may be delivered to a patient via a fluid path set. The spike typically has a pointed tip operative for piercing a sealing membrane at the outlet port of the medical container. When the spike is inserted into the outlet port, the sealing membrane is pierced by the pointed tip and fluid from the container can flow from the outlet port to the patient via the fluid path set.

In certain applications, it is important that a sterile connection is made between the container, the spike, and the fluid path set. Examples of areas where sterile connections are desirably made, include, without limitation, intravenous infusions, the processing of blood and its fractions, cell cultures, and the mixing of sterile solutions.

Many types of spikes have been proposed within the prior art for use with various medical containers. Typically, when a new spike is inserted into the outlet port of the medical container, the medical practitioner must ensure that a sterile connection is made. Various types of sterilization techniques also have been suggested, alone or in conjunction with various spike connectors. The sterility of the initial connection of the spike with the medical container can be ensured, for example, by the design of the spike and the outlet port or by swabbing the spike and/or the outlet port with a sterilizing fluid, such as alcohol. Typical spikes are designed such that once the spike is inserted into the medical container, it can be easily removed therefrom. While it is desirable to discard the spike after each use, when the spike is used with multi-patient fluid path sets, the spike can be reused and connected to another medical container. However, each new connection between the spike and the outlet port of the medical container must be sterile. Because sterilization of the spike and/or the outlet port requires handling by a human operator, it is susceptible to human error. This can lead to a contaminated connection between the spike and the medical container and possible infection of one or more patients.

While conventional spikes for medical containers are known in the medical field, improved attachment devices for medical containers continue to be in demand. Additionally, improved attachment devices for medical containers having a safety feature to prevent reuse of the attachment device are also desired in the medical field.

SUMMARY OF DISCLOSURE

In view of the disadvantages of the existing spikes for medical containers, there is a need in the art for an improved attachment device that overcomes the deficiencies of the prior art. There is an additional need for an improved attachment device for a medical container that limits or prevents reuse of the attachment device. A further need exists in the art for an improved attachment device for a medical container having one or more elements adapted for preventing the withdrawal of the attachment element from the medical container after an initial connection is made.

In one embodiment, an attachment device for connecting a fluid path set to a medical container may include a body having a pointed distal end and a proximal end configured for connecting to the fluid path set and one or more removable elements configured to removably connect to the pointed distal end of the body. The one or more removable elements may have a distal end configured for extending through a membrane of the medical container. At least one fluid channel may extend along a longitudinal axis of the body and the one or more removable elements. The at least one fluid channel may be configured for delivering a medical fluid between the medical container and the fluid path set. At least one retaining element may project from the body and each of the removable elements. The at least one retaining element on a most distal removable element may be configured for non-removably retaining the most distal removable element of the attachment device within the medical container after the attachment device is connected to the medical container, while allowing disengagement and removal of the body and any proximal removable elements. The one or more removable elements may be stacked in a nested arrangement on the distal end of the body. The attachment device may further include a locking mechanism between the body and a first removable element and between successive removable elements. The locking mechanism may include at least one barb extending radially outward from the body and each of the removable elements. The barb may further include a groove on an outer surface of the barb and a tab on an inner surface of the tab. The groove of a first removable element may be configured to receive the tab of a second removable element stacked on top of the first removable element and lock the removable elements such that they cannot be separated without disengaging the tab from the groove. The at least one retaining element of the most distal removable element may be deflectable toward the body when the attachment device is moved in an insertion direction through the membrane of the medical container. The deflectable retaining element of the most distal removable element may be deflectable away from the body when the attachment device is moved in a withdrawal direction through the membrane such that the most distal removable element is detached from the body and retained within the medical container.

In another embodiment, an attachment device for connecting a fluid path set to a medical container may include a body having a pointed distal end and a proximal end configured for connecting to a fluid path set. The pointed distal end may be configured for puncturing a membrane of the medical container. The attachment device may further include one or more fluid channels extending along a longitudinal axis of the body. The at least one fluid channel may be configured for delivering a medical fluid between the medical container and the fluid path set. At least one deflectable retaining element may project from the body of the attachment device between the distal end and the proximal end. The at least one retaining element may be configured for non-removably retaining the attachment device and the medical container after the attachment device is connected to the medical container.

In a further embodiment, the at least one deflectable retaining element may have a first end connected to the body and a second end extending radially outward from the body. The deflectable retaining element may be deflectable toward the body when the attachment device is moved in an insertion direction through the membrane, and the deflectable retaining element may be deflectable away from the body when the attachment device is moved in a withdrawal direction through the membrane. At least one recess may be provided on the body, wherein the at least one recess is configured for receiving the at least one deflectable retaining element when the deflectable retaining element is in the deflected configuration.

In another embodiment, a connector may be provided at the proximal end of the attachment device, wherein the connector is configured for connecting to the fluid path set. A gripping surface may be provided with one or more ribs extending radially outward from the body at the proximal end. A tab may be provided distal to the gripping surface, wherein the tab extends radially outward past at least a portion of the gripping surface. An auxiliary port, located proximal to the tab, may extend through the body in fluid connection with the at least one fluid channel. The auxiliary port may comprise a removable cap element configured for enclosing the auxiliary port. At least one barb may extend radially outward from the body and circumscribe a circumference of the body, wherein the at least one barb is angled relative to a longitudinal axis of the body such that the at least one barb is pointed from the proximal end toward the distal end.

In yet another embodiment, an attachment device for connecting a fluid path set to a medical container may include a body having a pointed distal end configured for extending through a membrane of the medical container and a proximal end configured for connecting to the fluid path set. The attachment device may further include at least one fluid channel extending along a longitudinal axis of the body between the distal end and the proximal end. The at least one fluid channel may be configured for flowing a medical fluid between the medical container and the fluid path set. At least one deflectable retaining element may extend outward from the body between the distal end and the proximal end, and at least one barb may extend radially outward from the body and circumscribe a circumference of the body. The at least one deflectable retaining element and the at least one barb may be configured for non-removably retaining the attachment device with the medical container after the attachment device is connected to the medical container. The deflectable retaining element may be deflectable toward the body when the attachment device is moved in an insertion direction through the membrane and the deflectable retaining element is deflectable away from the body when the attachment device is moved in a withdrawal direction through the membrane. The at least one barb may be angled relative to a longitudinal axis of the body such that the at least one barb is pointed from the proximal end toward the distal end.

These and other features and characteristics of the attachment device for a medical container, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION OF THE EMBODIMENTS

Figure 1:
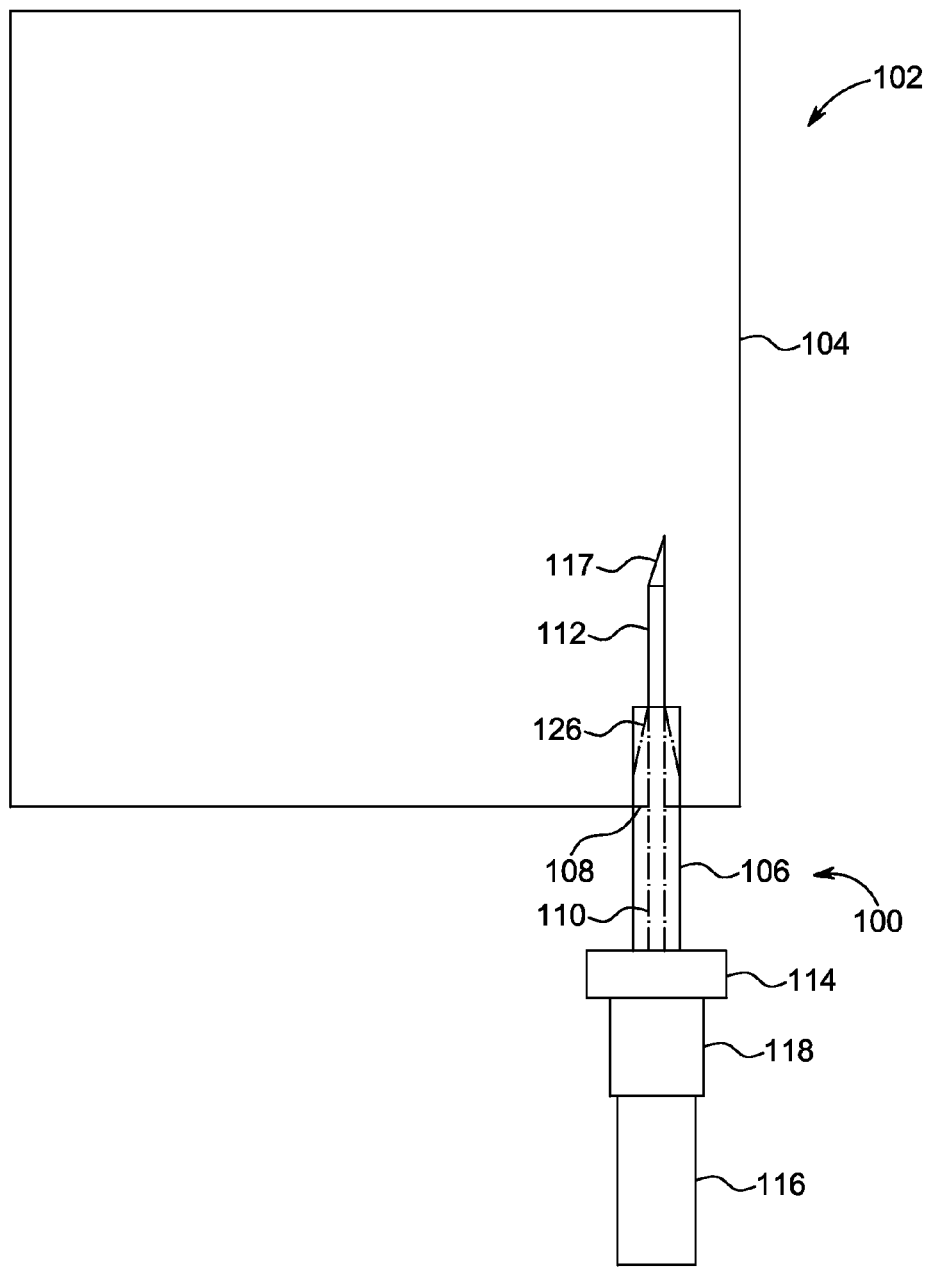
FIG. 1 is a front view of an attachment device in connection with a medical container and fluid path set.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

Referring to the drawings in which like reference characters refer to like parts throughout the several views thereof, the present disclosure is generally directed to an attachment device for a medical container, such as a bag, bottle or vial.

Referring initially to FIG. 1, an embodiment of an attachment device 100 is shown. The attachment device 100, as described herein, is intended for connection to a medical container 102, as will be readily apparent to those skilled in the medical art. The medical container 102 desirably has a sealed interior for containing a powdered or liquid medicament. In one embodiment, the attachment device 100 is adapted for use with a bag-type medical container 102. However, this use is intended to be non-limiting and attachment device 100 has applications with all medical containers in general. For example, the attachment device 100 may be used with a vial or bottle having a piercable rubber septum sealing the vial interior.

With continuing reference to FIG. 1, the medical container 102 includes a container body 104 having an interior volume at least partially filed with a powdered or liquid medicament (not shown). The medical container 102 further includes an outlet port 106 extending between the container interior and the container exterior. The outlet port 106 is adapted for connecting to the attachment device 100, as will be described herein. A sealing membrane 108 extends across the outlet port 106 for sealing the medical fluid within the interior volume of the medical container 102. For example, the sealing membrane 108 may be a resilient rubber septum configured for having an intimate sealing engagement with the attachment device 100 as the attachment device 100 is inserted from the container exterior to the container interior through the sealing membrane 108. Desirably, the sealing membrane 108 is flexible, inert, impermeable to fluid, and readily piercable by the attachment device 100. The sealing membrane 108 may be breakable by the attachment device 100. In another embodiment, the sealing membrane 108 may have a rubber septum with a tear-off seal (not shown), or the like.

The attachment device 100 includes a body 110 having a pointed distal end 112 configured for extending through the membrane 108 of the medical container 102. The body 110 further includes a proximal end 114 configured for connecting to a fluid path set 116. In various embodiments, the fluid path set 116 may be a needleless syringe, IV tubing, or any other fluid transfer member for transferring medicament or other fluid to and from the medical container 102. The body 110 is generally hollow with a fluid channel 117 extending between the distal end 112 and the proximal end 114. The fluid channel 117 is configured for delivering the medicament between the interior of the medical container 102 and the fluid path set 116. The attachment device 100 is removably connectable to the fluid path set 116 using, for example, a Luer-type connector. In one embodiment, the attachment device 100 has a male-type fitting that is configured for connecting to a female-type fitting of the fluid path set 116. Alternatively, the attachment device 100 has a female-type fitting that is configured for connecting to a male-type fitting of the fluid path set 116.

In one embodiment, the attachment device 100 is made from a plastic material, such as polypropylene, polyethylene, or other suitable biocompatible material. The material may be substantially rigid and is desirably medically inert. In other embodiments, the attachment device 100 is made from a metal material, such as stainless steel or other medically inert metal or metal alloy, to allow sterilization in an autoclave or a similar device. One of ordinary skill in the art will understand that the attachment device 100 may be made from any plastic or metal material, or a combination thereof, without being limited to the examples disclosed herein.

With continuing reference to FIG. 1, at least one deflectable retaining element 126 projects from the body 110 of the attachment device 100 between the distal end 112 and the proximal end 114. The at least one deflectable retaining element 126 is configured for non-removably retaining the attachment device 100 with the medical container 102 after the attachment device 100 is connected to the medical container 102. In one embodiment, the at least one deflectable retaining element 126 engages a sidewall of the outlet port 106 such that the attachment device 100 can be inserted into the outlet port 106 but cannot be removed therefrom due to the at least one deflectable retaining element 126 engaging the sidewall of the outlet port 106. Alternatively, or in addition, the at least one retaining element 126 extends past the outlet port 106 into the interior volume of the medical container 102 such that the attachment device 100 can be inserted into the outlet port 106 but cannot be removed therefrom due to the at least one deflectable retaining element 126 being deflected away from the body 110. In another embodiment, the at least one deflectable retaining element 126 is configured to allow insertion of the attachment device 100 through the sealing membrane 108 but prevent withdrawal of the attachment device 100 once inserted through the sealing membrane 108.

With reference to FIGS. 2A-15, the attachment device 100 is illustrated in accordance with various embodiments, each of which will be described in greater detail herein.

Referring to FIGS. 2A-2D, the attachment device 100a is shown in accordance with a first embodiment. The attachment device 100a includes a body 110a having a pointed distal end 112a configured for extending through the membrane 108 of the medical container 102 (shown in FIG. 1). The body 110a further includes a proximal end 114a configured for connecting to a fluid path set 116 (shown in FIG. 1). The body 110a is generally hollow with a fluid channel 117a extending between the distal end 112a and the proximal end 114a. The fluid channel 117a is configured for delivering the medical fluid between the interior of the medical container 102 and the fluid path set 116.

The attachment device 100a is removably connectable to the fluid path set 116 using, for example, a Luer-type connector 118a. The Luer-type connector 118a on the attachment device 100a may be a male or female end configured for removable connection with the corresponding female or male end, respectively, on the fluid path set 116. One of ordinary skill in the art will understand that the Luer-type connector 118a may be replaced with any other known connector for connecting the attachment device 100a to the fluid path set 116.

With continuing reference to FIGS. 2A-2D, the attachment device 100a further includes a gripping surface 120a having one or more ribs that facilitate handling of the attachment device 100a during insertion into the medical container 102. The gripping surface 120a is provided at the proximal end 114a. In one embodiment, the gripping surface 120a has at least one flattened portion to prevent rotation of the attachment device 100a during insertion through the membrane 108 or during connection to the fluid path set 116. The gripping surface 120a may be ergonomically shaped to conform to the shape of the user's fingers to facilitate handling of the attachment device 100a. A tab 122a may be provided distally of the gripping surface 120a to prevent accidental contamination of the attachment device 100a and/or distal portion of body 110a by contact with a non-sterilized surface. The tab 122a extends radially outward and substantially perpendicular to a longitudinal axis of the body 110a. The tab 122a may be removably attached or integrally formed with the attachment device 100a.

The attachment device 100a further includes an auxiliary port 124a at the proximal end 114a. The auxiliary port 124a is adapted for connection to a syringe (not shown) or other fluid transfer device for injecting a second medical fluid into or withdrawing a medical fluid from the medical container 102 through the attachment device 100a. The auxiliary port 124a connects to the fluid channel 117a extending along the longitudinal length of the attachment device 100a. The auxiliary port 124a may be oriented substantially perpendicular to the fluid channel 117a or it may be inclined at an angle relative to the fluid channel 117a. In one embodiment, the auxiliary port 124a may have a pierceable seal for sealing the auxiliary port 124a until the seal is pierced by the fluid transfer device. In other embodiments, auxiliary port 124a may include a removable cap element.

As shown in FIGS. 2A-2D, the attachment device 100a includes at least one retaining element 126a adapted to prevent withdrawal of the attachment device 100a from the outlet port 106 of the medical container 102. The at least one retaining element 126a includes at least one barb 128a extending radially outward from the body 110a. The at least one barb 128a extends around at least a part of the circumference of the body 110a. In one embodiment, the at least one barb 128a may extend around the entire circumference of the body 110a. The at least one barb 128a is angled relative to the longitudinal axis of the attachment device 100a such that the at least one barb 128a is pointed from the proximal end 114a toward the distal end 112a. The at least one barb 128a may be integrally formed with the body 110a. The at least one barb 128a is adapted to engage the sidewall of the outlet port 106 of the medical container 102 and to prevent withdrawal of the attachment device 100a after the attachment device 100a is inserted into the medical container 102. Alternatively, or in addition, the at least one barb 128a is configured to allow insertion of the attachment device 100a through the sealing membrane 108 but prevent withdrawal of the attachment device 100a once inserted through the sealing membrane 108.

The at least one retaining element 126a further includes at least one deflectable retaining element 130a, for example in the form of an expandable tab, provided at the distal end 112a. One end of the at least one radially or outwardly deflectable retaining element 130a is connected to the body 110a while the other end of the at least one deflectable retaining element 130a is movable relative to the body 110a. The at least one deflectable retaining element 130a may be formed separately from the body 110a and subsequently attached thereto. Alternatively, the at least one deflectable retaining element 130a may be integrally formed with the body 110a. The at least one deflectable retaining element 130a is adapted to expand against the sidewall of the outlet port 106 or expand outside the outlet port 106 when the distal end 112a is inserted through the outlet port 106 and into the interior volume of the medical container 102. In an initial state, such as before being inserted through the membrane 108, the at least one deflectable retaining element 130a extends radially outward relative to the longitudinal length of the body 110a, as shown in FIGS. 2A-2D.

The at least one deflectable retaining element 130a is adapted to prevent withdrawal of the attachment device 100a after the attachment device 100a is inserted into the medical container 102. For example, the at least one deflectable retaining element 130a may be configured for being pressed or deflected against the body 110a during insertion of the attachment device 100a through the membrane 108 and to expand radially outward once the portion of the body 110a where the at least one deflectable retaining element 130a is provided passes through the membrane 108. When the attachment device 100a is advanced in an insertion direction (i.e., in a direction from the proximal end 114a toward the distal end 112a), the at least one deflectable retaining element 130a is configured to be deflected radially inward toward the body 110a as it is passed through the membrane 108. When the attachment device 100a is retracted in a withdrawal direction (i.e., in a direction from the distal end 112a toward the proximal end 114a), the at least one deflectable retaining element 130a is configured to be deflected radially outward away from the body 110a. Because the at least one deflectable retaining element 130a is pointed from the proximal end 114a toward the distal end 112a, withdrawal of the attachment device 100a from the membrane 108 is prevented. The at least one deflectable retaining element 130a deflects radially outward such that it cannot be passed through the same opening through which the body 110a is inserted into the membrane 108. In certain embodiments, a recess 134a may be provided on an outer sidewall of the body 110a to receive the at least one deflectable retaining element 130a during insertion of the attachment device 100a through the membrane 108. In this manner, the body 110a has a substantially tubular shape to facilitate insertion through the membrane 108. In one embodiment, a pair of opposing deflectable retaining element 130a may be provided. While the at least one deflectable retaining element 130a is shown in FIGS. 2A-2D as being located distally from the at least one barb 128a, in an alternative embodiment, the at least one deflectable retaining element 130a may be provided proximally relative to the at least one barb 128a.

Figure 2A:
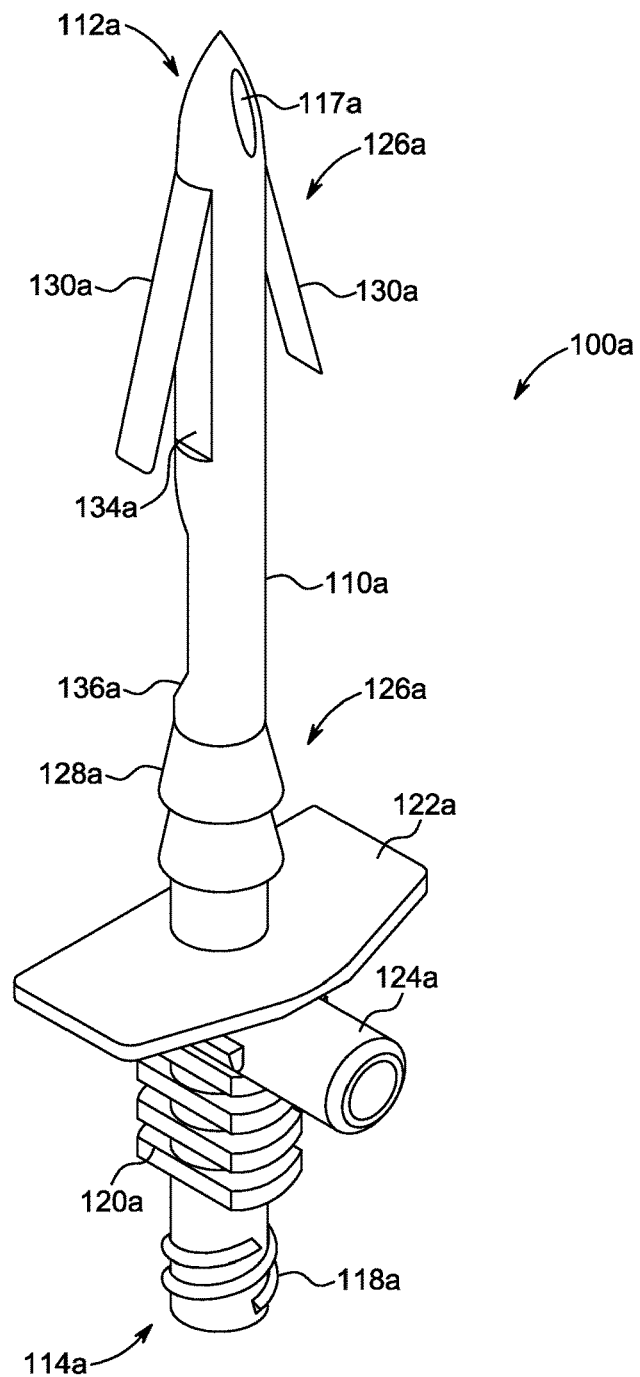
FIG. 2A is a front perspective view of an attachment device for a medical container in accordance with a first embodiment.
Figure 2B:
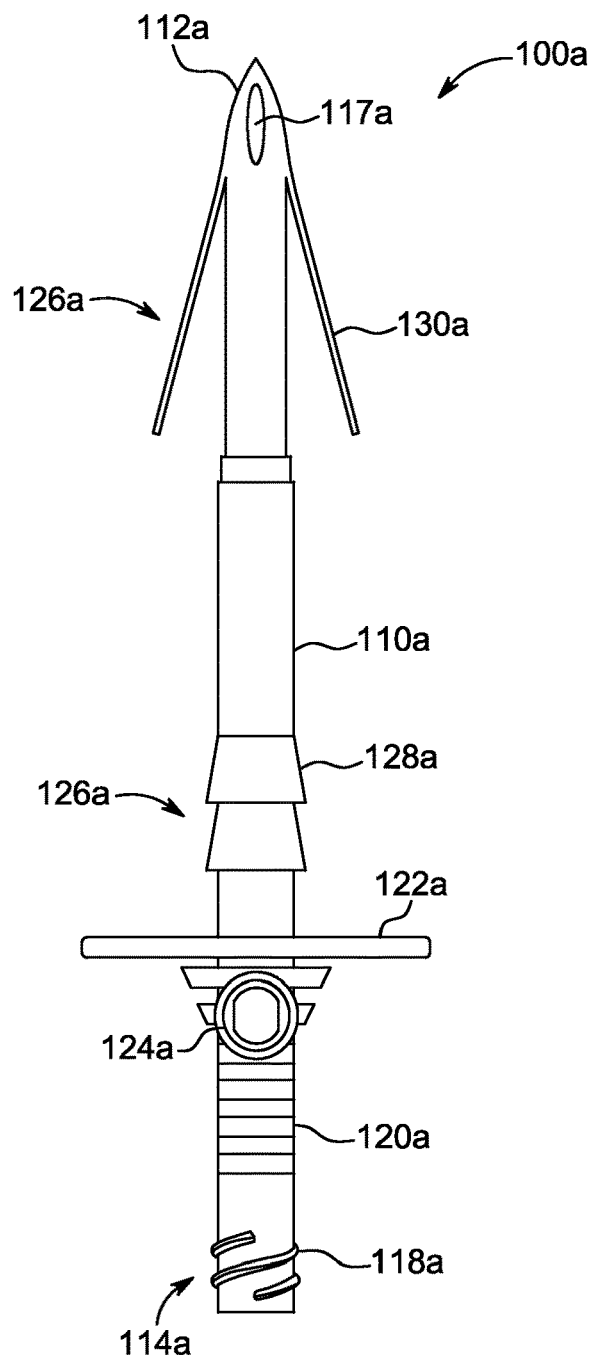
FIG. 2B is a front view of the attachment device shown in FIG. 2A.
Figure 2C:
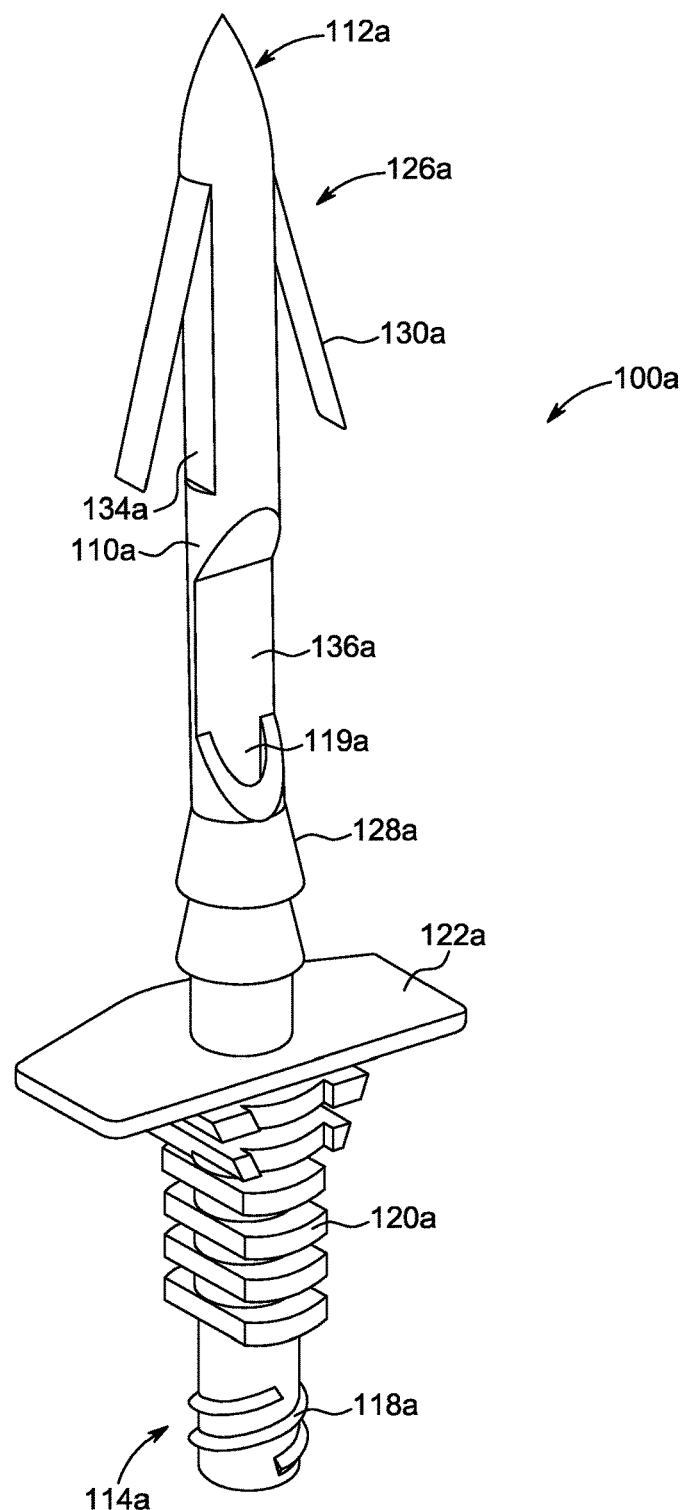
FIG. 2C is a rear perspective view of the attachment device shown in FIG. 2A.
Figure 2D:
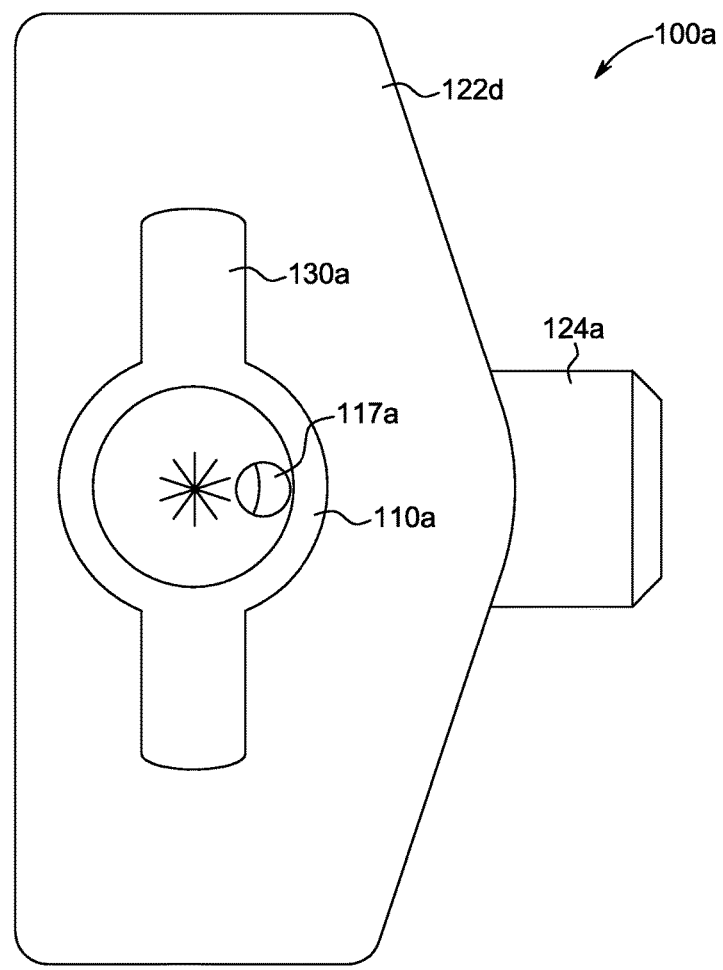
FIG. 2D is a top view of the attachment device shown in FIG. 2A.
Figure 3A:
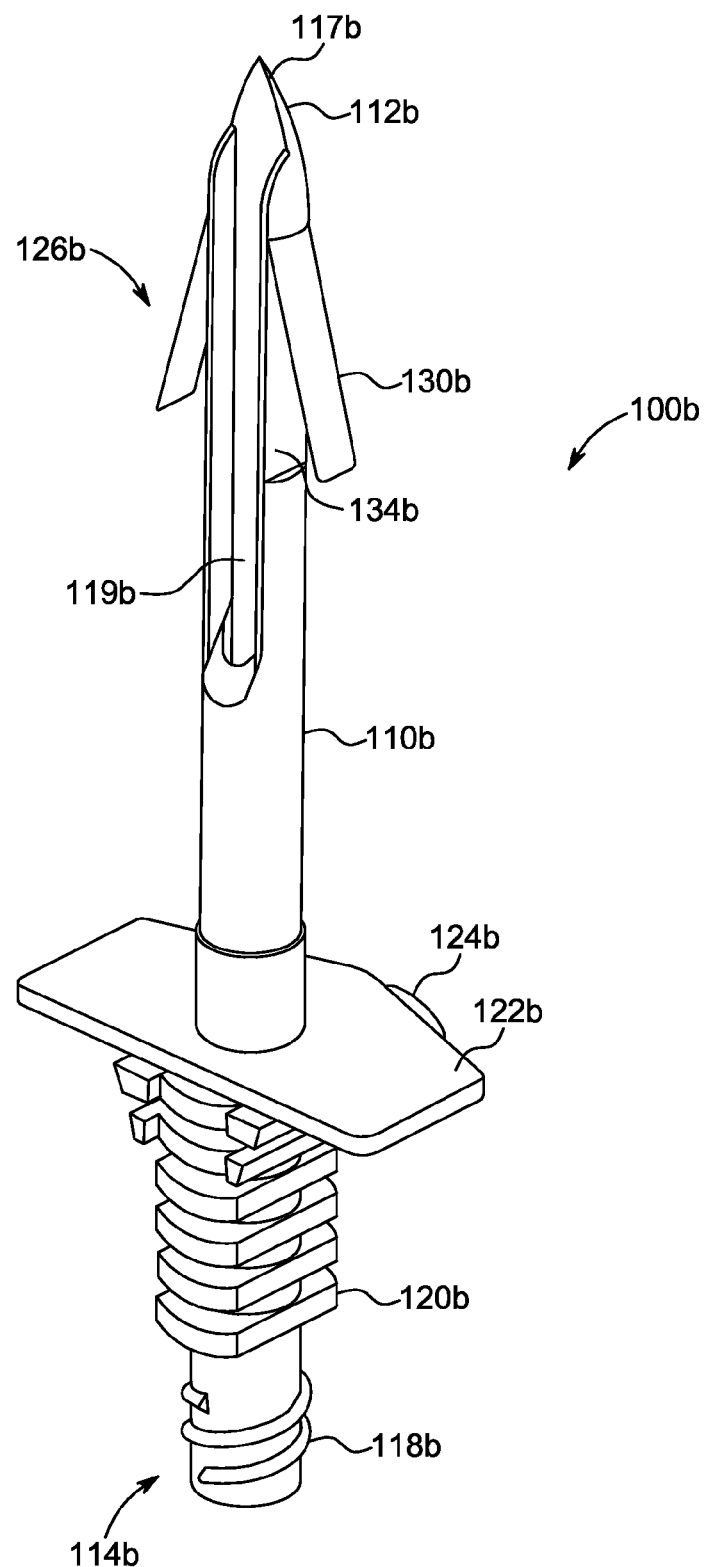
FIG. 3A is a rear perspective view of an attachment device for a medical container in accordance with a second embodiment.
Figure 3B:
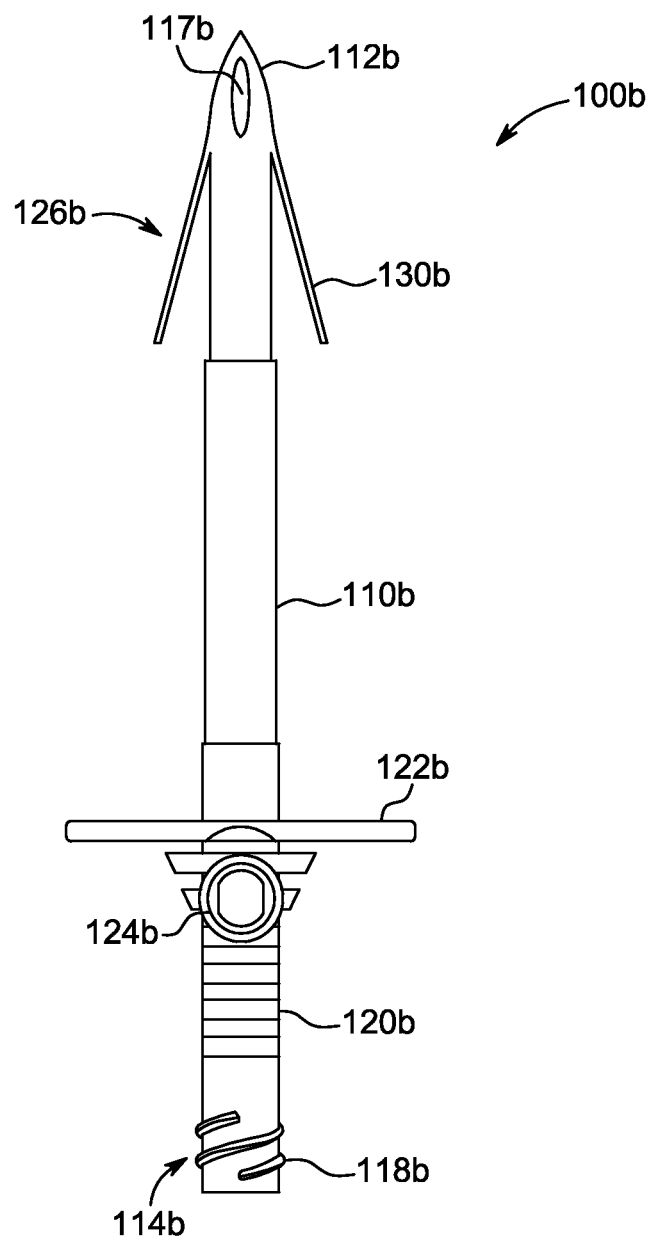
FIG. 3B is a front view of the attachment device shown in FIG. 3A.
Figure 3C:
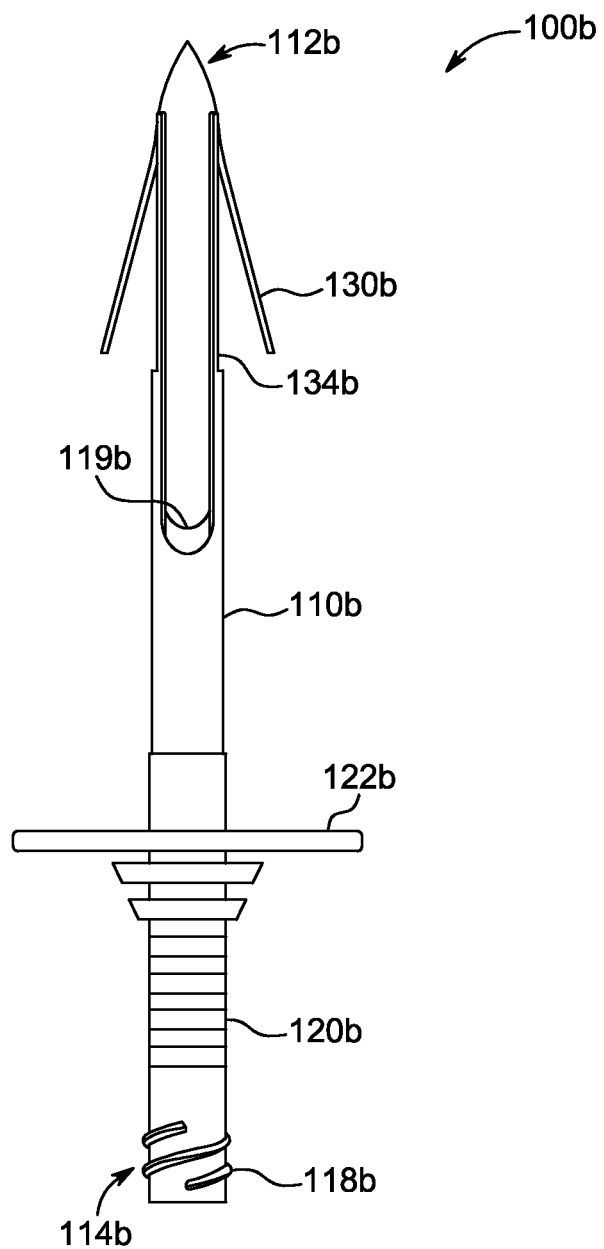
FIG. 3C is a rear side view of the attachment device shown in FIG. 3A.
Figure 3D:
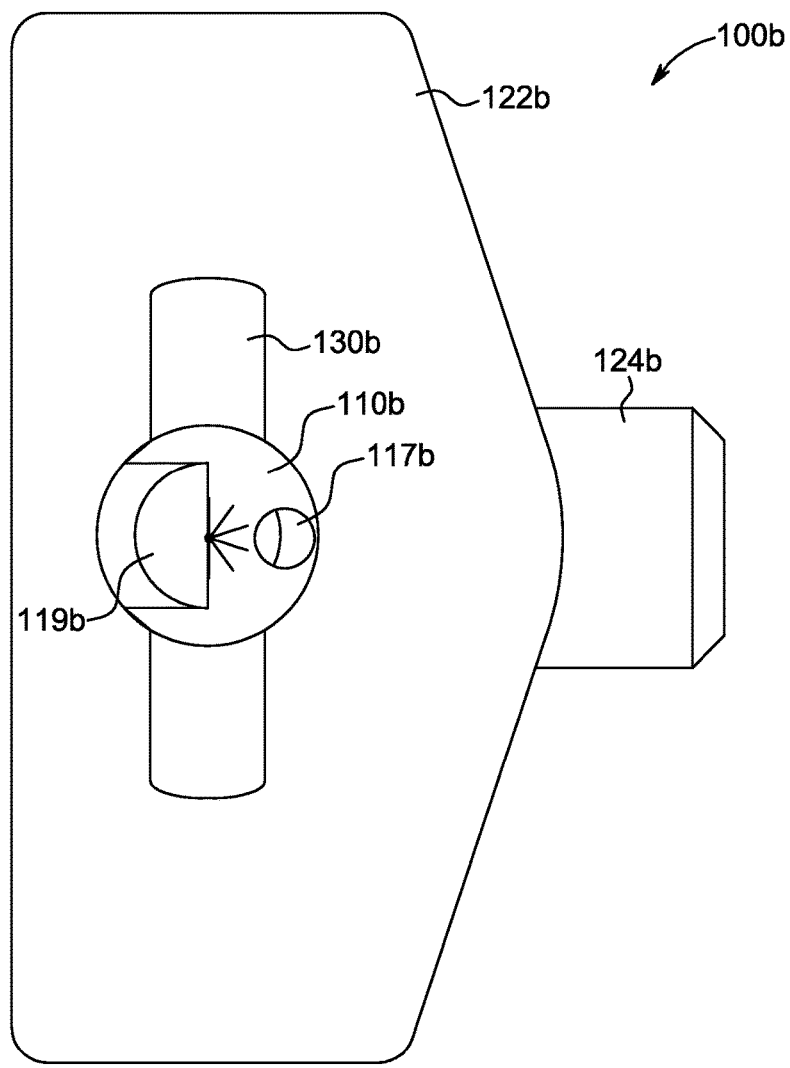
FIG. 3D is a top view of the attachment device shown in FIG. 3A.

With reference to FIG. 2C, the attachment device 100a may have a second fluid channel 119a that extends from the proximal end 114a through a portion of the body 110a. The second fluid channel 119a may be an air inlet channel that allows the void created by a departing fluid to be replaced with outside air. The second fluid channel 119a may have an air filter (not shown) to allow air to pass therethrough while preventing the passage of liquid. The second fluid channel 119a may extend through a depression 136a provided on a central portion of the body 110a. In one embodiment, the second fluid channel 119a is substantially parallel to the fluid channel 117a.

Referring to FIGS. 3A-3D, the attachment device 100b is shown in accordance with a second embodiment. The attachment device 100b is substantially similar to the attachment device 100a described with reference to FIGS. 2A-2D above. Reference numerals 110b-124b in FIGS. 3A-3D are used to illustrate equivalent components as reference numerals 110a-124a in FIGS. 2A-2D. The retaining element 126b includes at least one deflectable retaining element 130b, for example in the form of an expandable tab, provided at the distal end 112b. Similar to the at least one deflectable retaining element 130a shown in FIGS. 2A-2D, one end of the at least one deflectable retaining element 130b is connected to the body 110b while the other end of the at least one deflectable retaining element 130b is movable radially or outwardly movable or expandable relative to the body 110b. The at least one deflectable retaining element 130b is adapted to prevent withdrawal of the attachment device 100b after the attachment device 100b is inserted into the medical container 102 (shown in FIG. 1). For example, the at least one deflectable retaining element 130b may be configured for being pressed or deflected against the body 110b during insertion of the attachment device 100b through the membrane 108 (shown in FIG. 1) and to expand radially outward once the portion of the body 110b where the at least one deflectable retaining element 130b is provided passes through the membrane 108. Because the at least one deflectable retaining element 130b is pointed from the proximal end 114b toward the distal end 112b, withdrawal of the attachment device 100b from the membrane 108 is prevented. The at least one deflectable retaining element 130b deflects radially outward such that it cannot be passed through the same opening through which the body 110b is inserted into the membrane 108. In certain embodiments, a recess 134b may be provided on an outer sidewall of the body 110b to receive the at least one deflectable retaining element 130b during insertion of the attachment device 100b through the membrane 108. In this manner, the body 110b has a substantially tubular shape to facilitate insertion through the membrane 108. In one embodiment, a pair of opposing deflectable retaining element 130b may be provided.

Figure 4A:
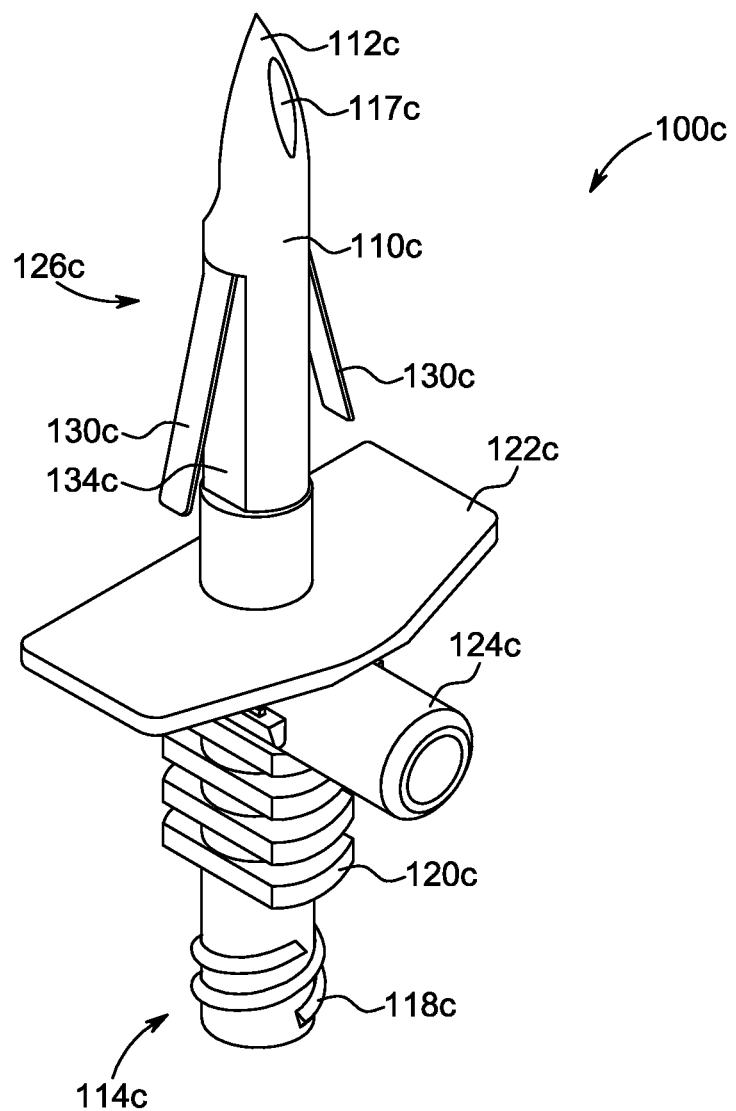
FIG. 4A is a front perspective view of an attachment device for a medical container in accordance with a third embodiment.
Figure 4B:
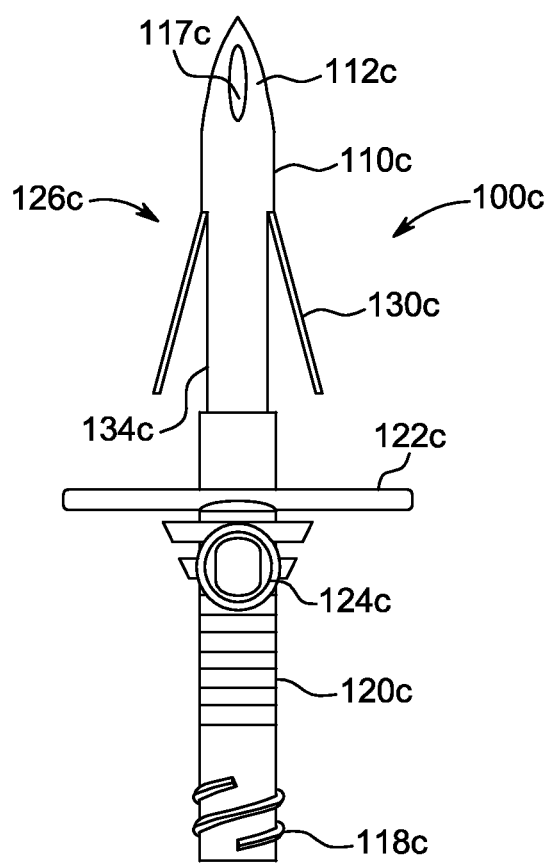
FIG. 4B is a front view of the attachment device shown in FIG. 4A.

Referring to FIGS. 4A-4B, the attachment device 100c is shown in accordance with a third embodiment. The attachment device 100c is substantially similar to the attachment device 100a described with reference to FIGS. 2A-2D above. Reference numerals 110c-124c in FIGS. 4A-4B are used to illustrate equivalent components as reference numerals 110a-124a in FIGS. 2A-2D. The retaining element 126c includes at least one deflectable retaining element 130c, for example in the form of an expandable tab, provided on the body 110c substantially between the distal end 112c and the proximal end 114c. Similar to the at least one deflectable retaining element 130a shown in FIGS. 2A-2D, one end of the at least one deflectable retaining element 130c is connected to the body 110c while the other end of the at least one deflectable retaining element 130c is radially or outwardly movable relative to the body 110c. The at least one deflectable retaining element 130c is adapted to prevent withdrawal of the attachment device 100c after the attachment device 100c is inserted into the medical container 102 (shown in FIG. 1). For example, the at least one deflectable retaining element 130c may be configured for being pressed or deflected against the body 110c during insertion of the attachment device 100c through the membrane 108 (shown in FIG. 1) and to expand radially outward once the portion of the body 110c where the at least one deflectable retaining element 130c is provided passes through the membrane 108. Because the at least one deflectable retaining element 130c is pointed from the proximal end 114c toward the distal end 112c, withdrawal of the attachment device 100c from the membrane 108 is prevented. The at least one deflectable retaining element 130c deflects radially outward such that it cannot be passed through the same opening through which the body 110c is inserted into the membrane 108. In certain embodiments, a recess 134c may be provided on an outer sidewall of the body 110c to receive the at least one deflectable retaining element 130c during insertion of the attachment device 100c through the membrane 108. In this manner, the body 110c has a substantially tubular shape to facilitate insertion through the membrane 108. In one embodiment, a pair of opposing deflectable retaining element 130c may be provided.

Figure 5A:
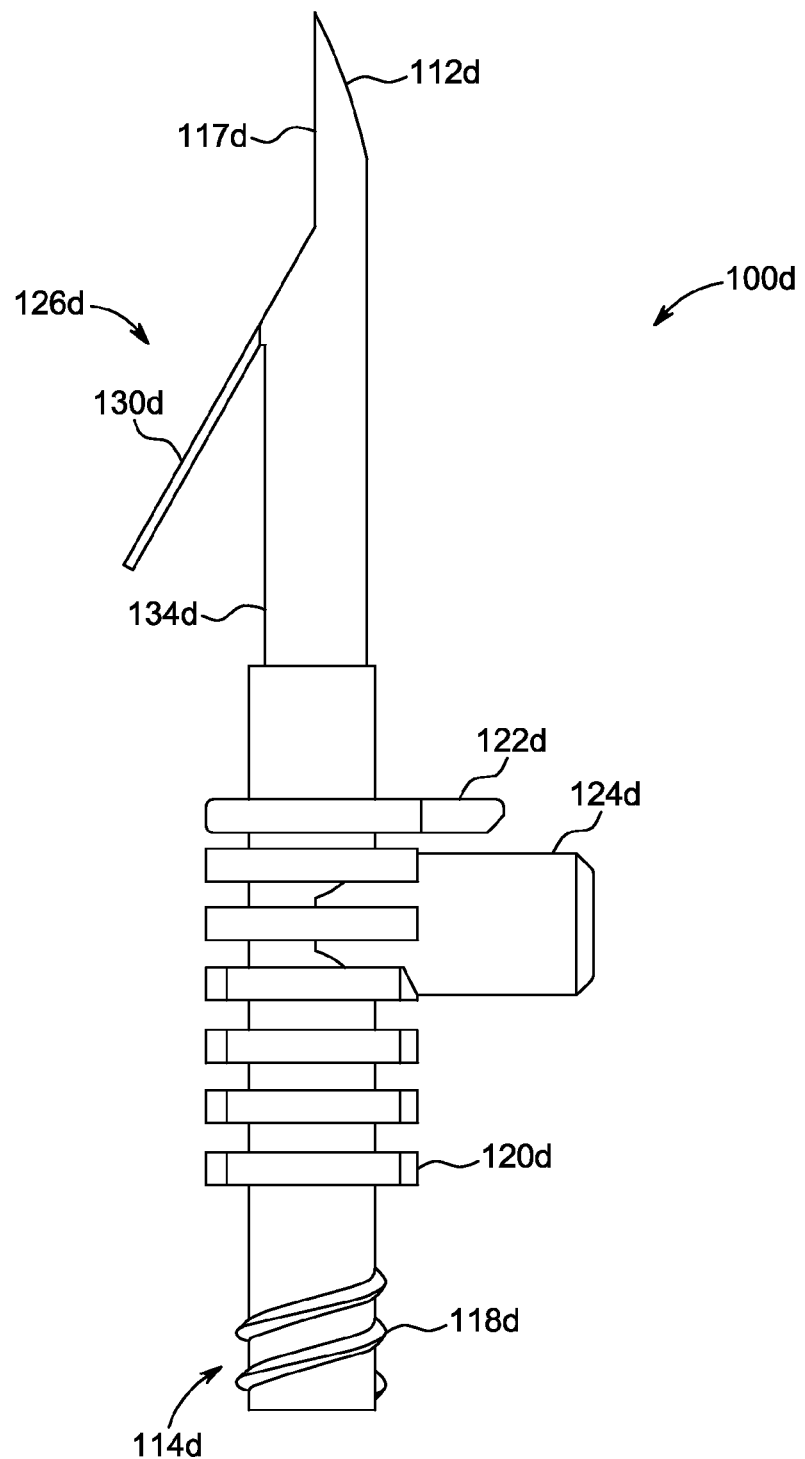
FIG. 5A is a side view of an attachment device for a medical container in accordance with a fourth embodiment.
Figure 5B:
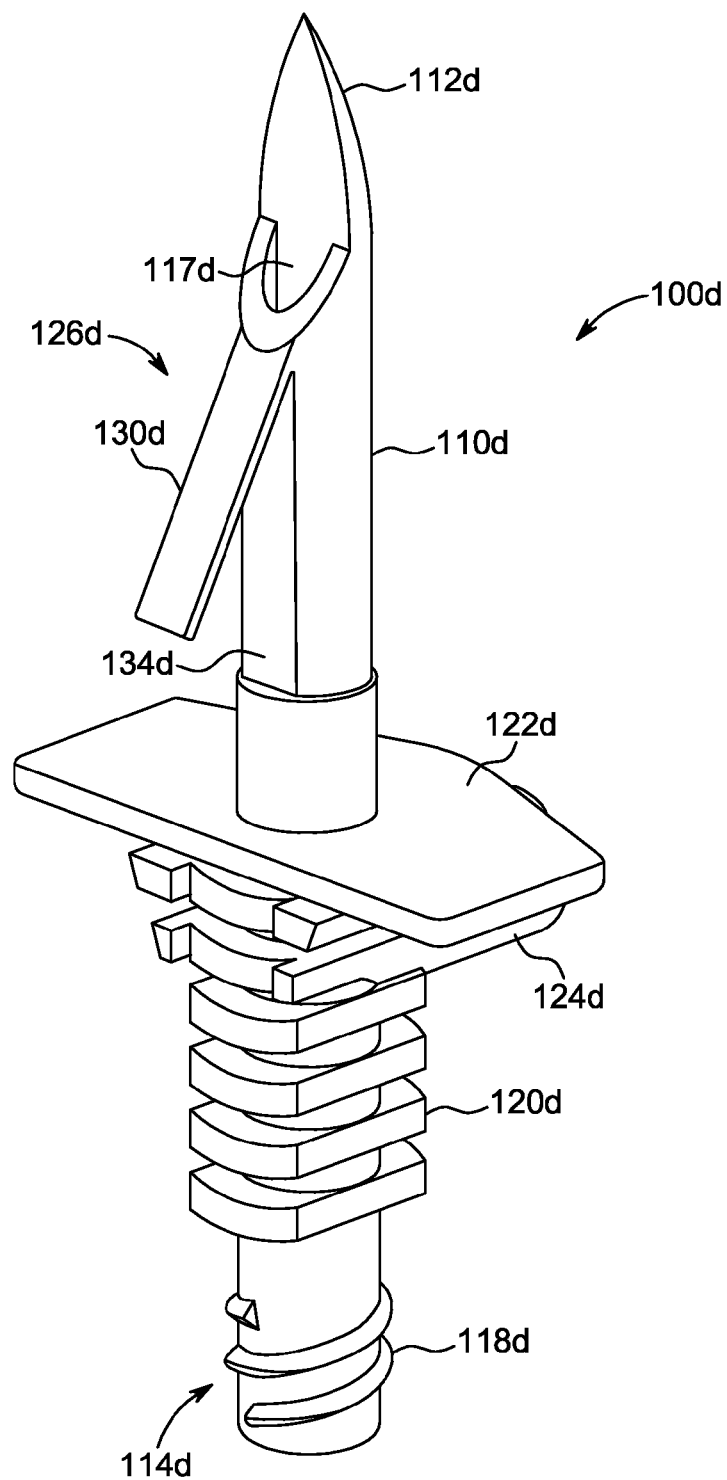
FIG. 5B is a rear perspective view of the attachment device shown in FIG. 5A.

Referring to FIGS. 5A-5B, the attachment device 100d is shown in accordance with a fourth embodiment. The attachment device 100d is substantially similar to the attachment device 100a described with reference to FIGS. 2A-2D above. Reference numerals 110d-124d in FIGS. 5A-5B are used to illustrate equivalent components as reference numerals 110a-124a in FIGS. 2A-2D. The retaining element 126d includes a single deflectable retaining element 130d, for example in the form of an expandable tab, provided at the distal end 112d. One end of the deflectable retaining element 130d is connected to the body 110d while the other end of the deflectable retaining element 130d is radially or outwardly movable or expandable relative to the body 110d. The deflectable retaining element 130d is adapted to prevent withdrawal of the attachment device 100d after the attachment device 100d is inserted into the medical container 102 (shown in FIG. 1). For example, the deflectable retaining element 130d may be configured for being pressed or deflected against the body 110b during insertion of the attachment device 100d through the membrane 108 (shown in FIG. 1) and to expand radially outward once the portion of the body 110b where the deflectable retaining element 130d is provided passes through the membrane 108. Because the one deflectable retaining element 130d is pointed from the proximal end 114d toward the distal end 112d, withdrawal of the attachment device 100d from the membrane 108 is prevented. The deflectable retaining element 130a deflects radially outward such that it cannot be passed through the same opening through which the body 110d is inserted into the membrane 108. In certain embodiments, a recess 134d may be provided on an outer sidewall of the body 110d to receive the deflectable retaining element 130d during insertion of the attachment device 100d through the membrane 108. In this manner, the body 110d has a substantially tubular shape to facilitate insertion through the membrane 108.

Figure 6A:
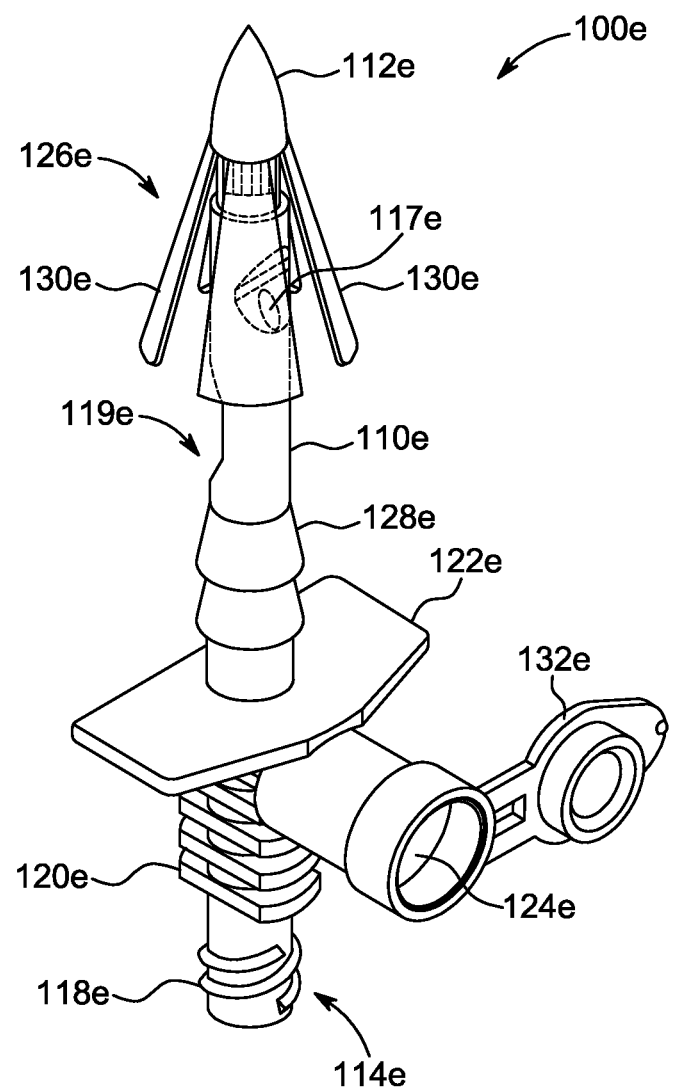
FIG. 6A is a front perspective view of an attachment device for a medical container in accordance with a fifth embodiment.
Figure 6B:
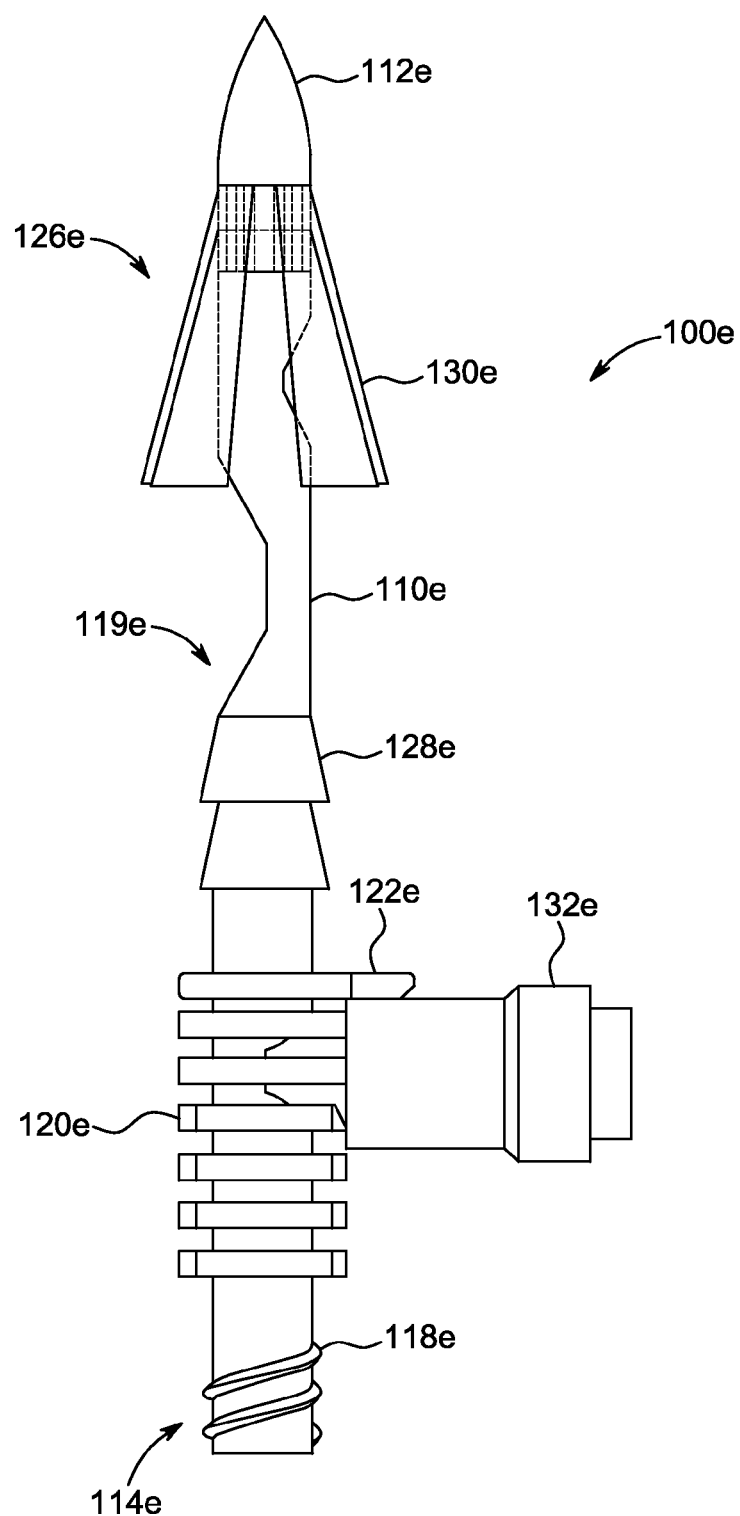
FIG. 6B is a side view of the attachment device shown in FIG. 6A.
Figure 6C:
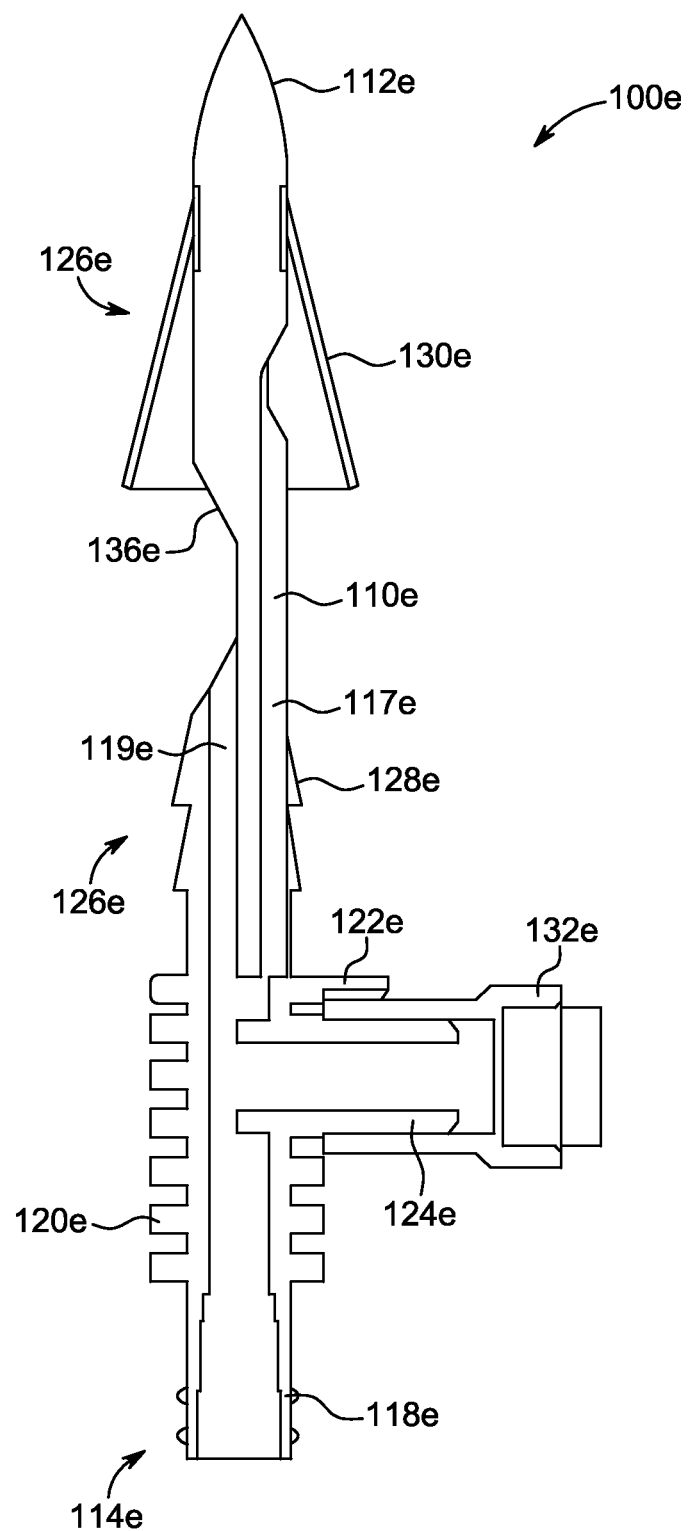
FIG. 6C is a cross-sectional view of the attachment device shown in FIG. 6B.

Referring to FIGS. 6A-6C, the attachment device 100e is shown in accordance with a fifth embodiment. The attachment device 100e is substantially similar to the attachment device 100a described with reference to FIGS. 2A-2D above. Reference numerals 110e-124e and 128e in FIGS. 6A-6C are used to illustrate equivalent components as reference numerals 110a-124a and 128a in FIGS. 2A-2D.

With reference to FIG. 6C, the auxiliary port 124e connects to the fluid channel 117e extending along the longitudinal length of the attachment device 100e. The auxiliary port 124e may be oriented substantially perpendicular to the fluid channel 117e or it may be inclined at an angle relative to the fluid channel 117e. In one embodiment, the auxiliary port 124e may have a piercable seal for sealing the auxiliary port 124e until the seal is pierced by the fluid transfer device. The attachment device 100e may comprise a second fluid channel 119e that extends from the proximal end 114e through a portion of the body 110e. The second fluid channel 119e may be an air inlet channel that allows the void created by a departing fluid to be replaced with outside air. The second fluid channel 119e may have an air filter (not shown) to allow air to pass therethrough while preventing the passage of liquid. The second fluid channel 119e may extend through a depression 136e provided on a central portion of the body 110e.

The attachment device 100e may further include a cap element 132e for selectively closing the auxiliary port 124e. The cap element 132e is configured for preventing access to the auxiliary port 124e when the cap element 132e is located in a closed position. In an open position, the cap element 132e is removed from the auxiliary port 124e such that the auxiliary port 124e may be accessed. The cap element 132e may be connected to at least a portion of the auxiliary port 124e, such as by a tether, to prevent the cap element 132e from being misplaced after it is removed from the auxiliary port 124e. Various embodiments of attachment devices 100a to 100i may also comprise an equivalent cap element for selectively closing auxiliary port 124a-124i.

With further reference to FIGS. 6A-6C, the at least one retaining element 126e further includes four deflectable retaining elements 130e, for example in the form of expandable tabs, provided at the distal end 112e. Each of the deflectable retaining elements 130e has one end connected to the body 110e while the other end extends radially outward relative to the body 110e. The deflectable retaining elements 130e are adapted to expand against the sidewall of the outlet port 106 or expand outside the outlet port 106 when the distal end 112e is inserted through the outlet port 106 and into the interior volume of the medical container 102 (shown in FIG. 1). In an initial state, such as before being inserted through the membrane 108, the deflectable retaining elements 130e extend radially outward relative to the longitudinal length of the body 110e, as shown in FIGS. 6A-6C.

Figure 7A:
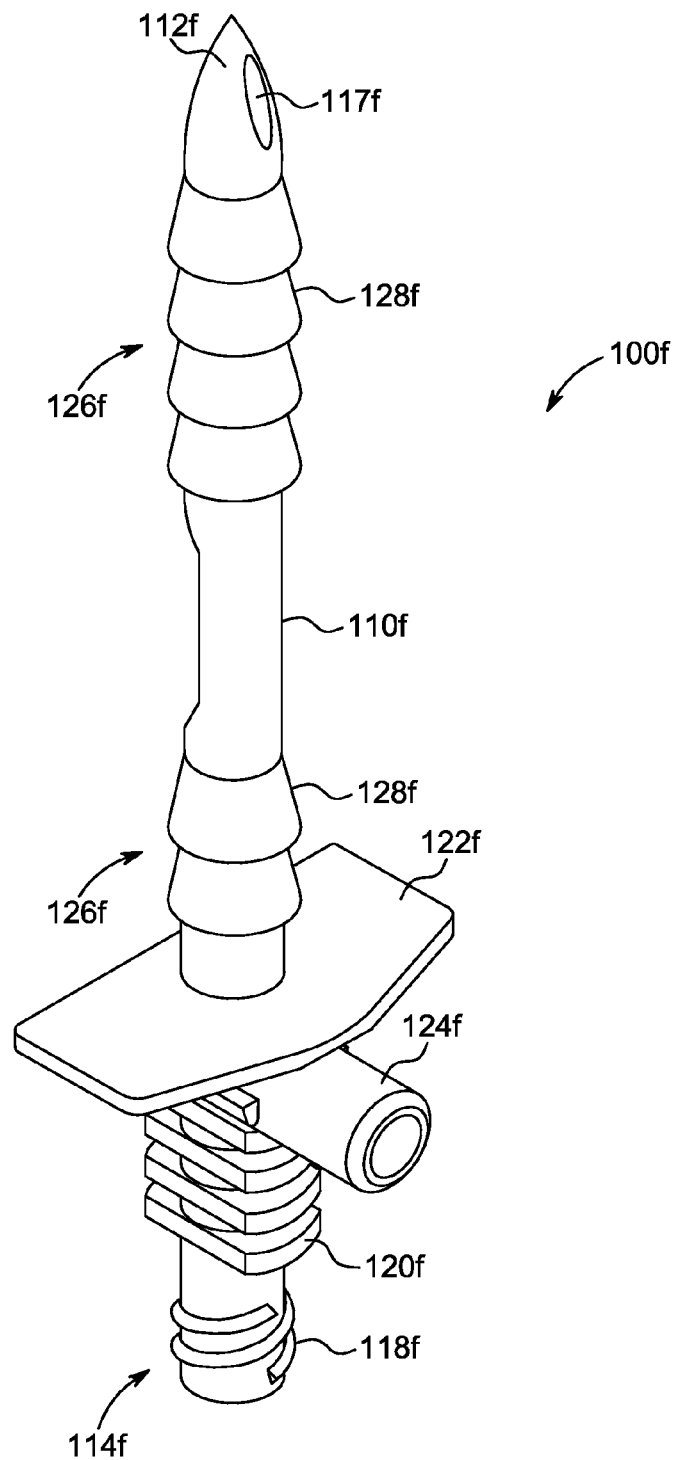
FIG. 7A is a front perspective view of an attachment device for a medical container in accordance with a sixth embodiment.
Figure 7B:
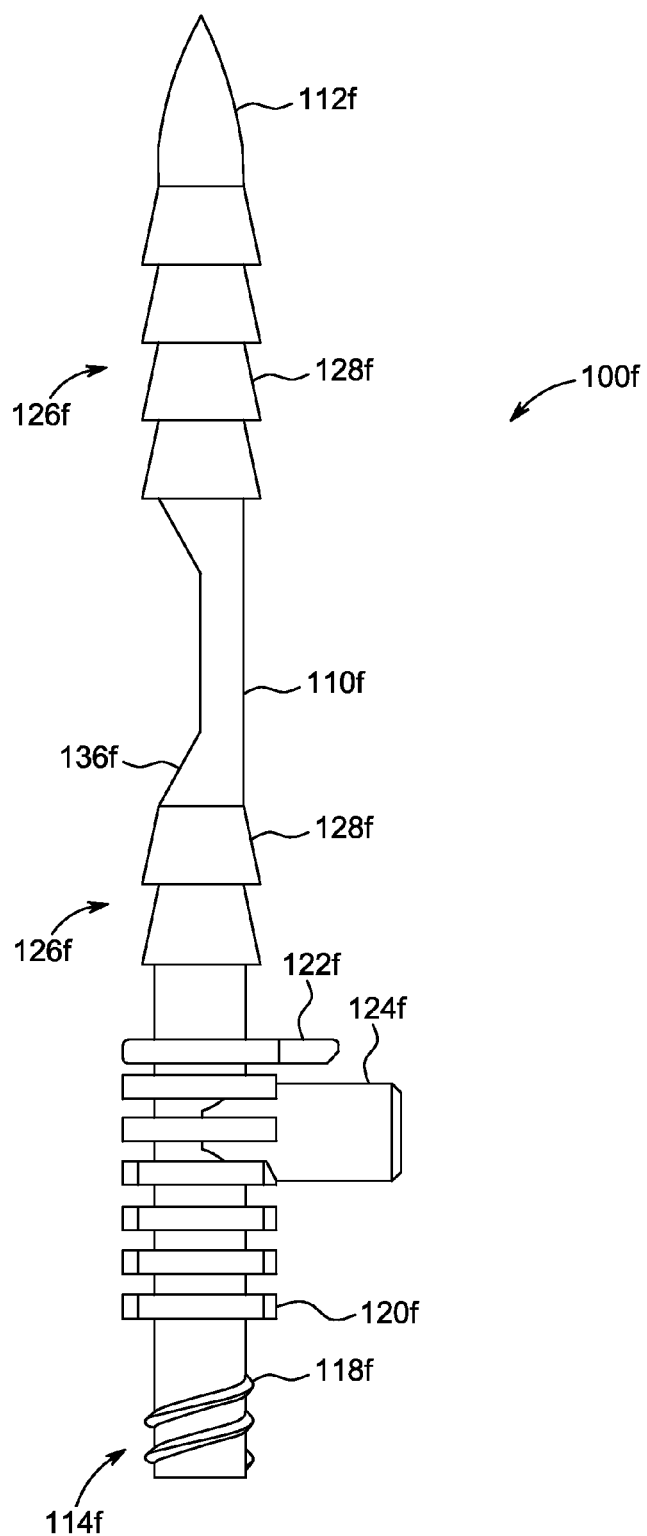
FIG. 7B is a side view of the attachment device shown in FIG. 7A.
Figure 7C:
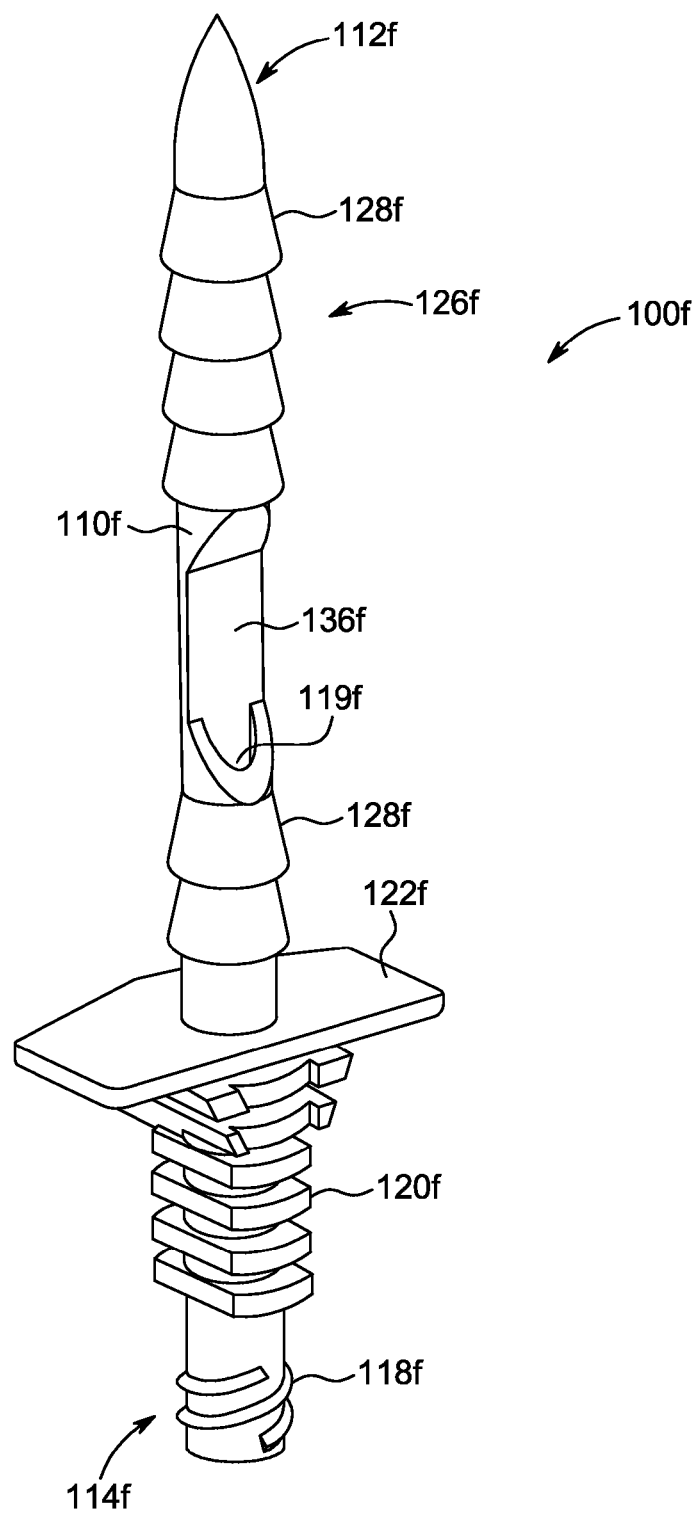
FIG. 7C is a rear perspective view of the attachment device shown in FIG. 7A.

Referring to FIGS. 7A-7C, the attachment device 100f is shown in accordance with a sixth embodiment. The attachment device 100f is substantially similar to the attachment device 100a described with reference to FIGS. 2A-2D above. Reference numerals 110f-124f in FIGS. 7A-7C are used to illustrate equivalent components as reference numerals 110a-124a in FIGS. 2A-2D. The at least one retaining element 126f includes a plurality of barbs 128f extending radially outward from the body 110f. Similar to the at least one barb 128a illustrated in FIGS. 2A-2D, each of the plurality of barbs 128f is angled relative to the longitudinal axis of the attachment device 100f such that the barbs 128f are pointed from the proximal end 114f toward the distal end 112f. The plurality of barbs 128f are separated such that one portion of the barbs 128f is located at the proximal end 114f while the other portion of the barbs 128f is located at the distal end 112f. The barbs 128f are adapted to engage the sidewall of the outlet port 106 of the medical container 102 and to prevent withdrawal of the attachment device 100f after the attachment device 100f is inserted into the medical container 102 (shown in FIG. 1). With reference to FIG. 7C, the attachment device 100f has a second fluid channel 119f that extends from the proximal end 114f through a portion of the body 110f. The second fluid channel 119f may be an air inlet channel that allows the void created by a departing fluid to be replaced with outside air. The second fluid channel 119f may have an air filter (not shown) to allow air to pass therethrough while preventing the passage of liquid. The fluid channel 119f extends through a depression 136f provided on a central portion of the body 110f.

Figure 8A:
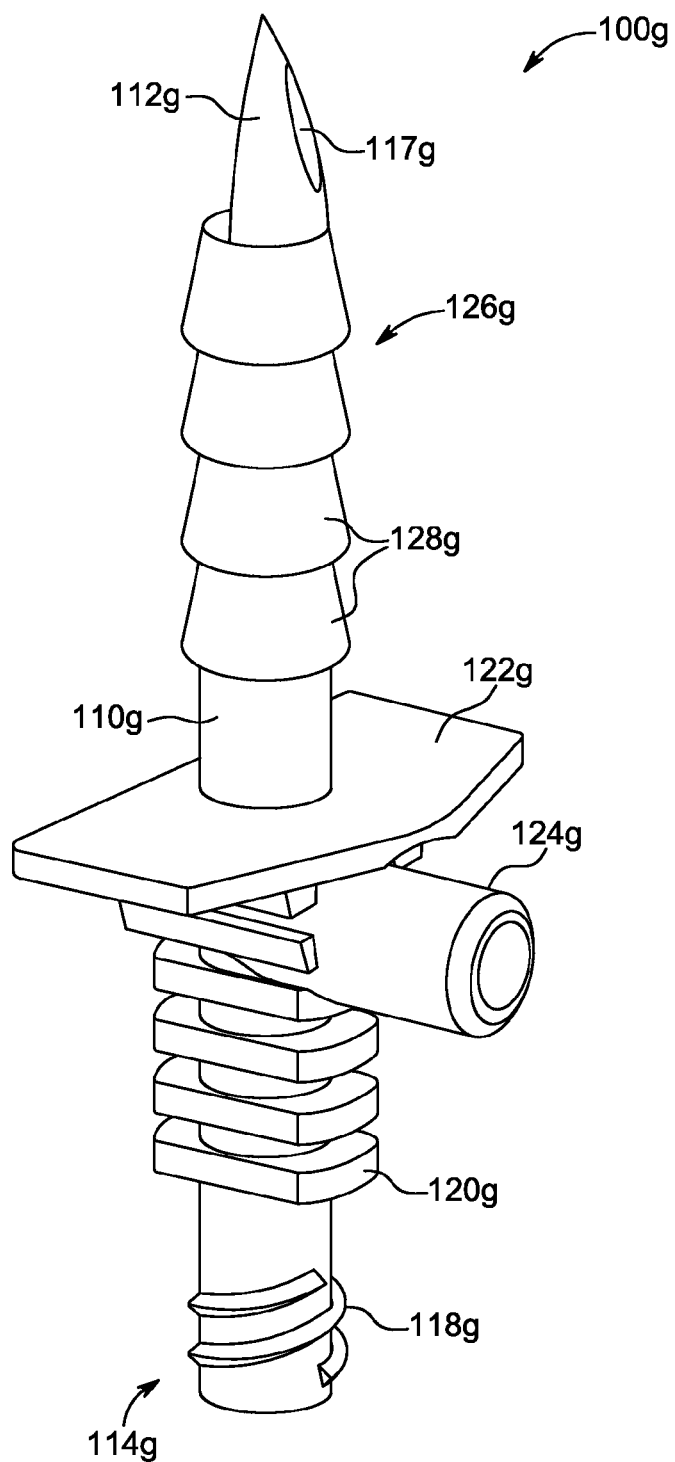
FIG. 8A is a front perspective view of an attachment device for a medical container in accordance with a seventh embodiment.
Figure 8B:
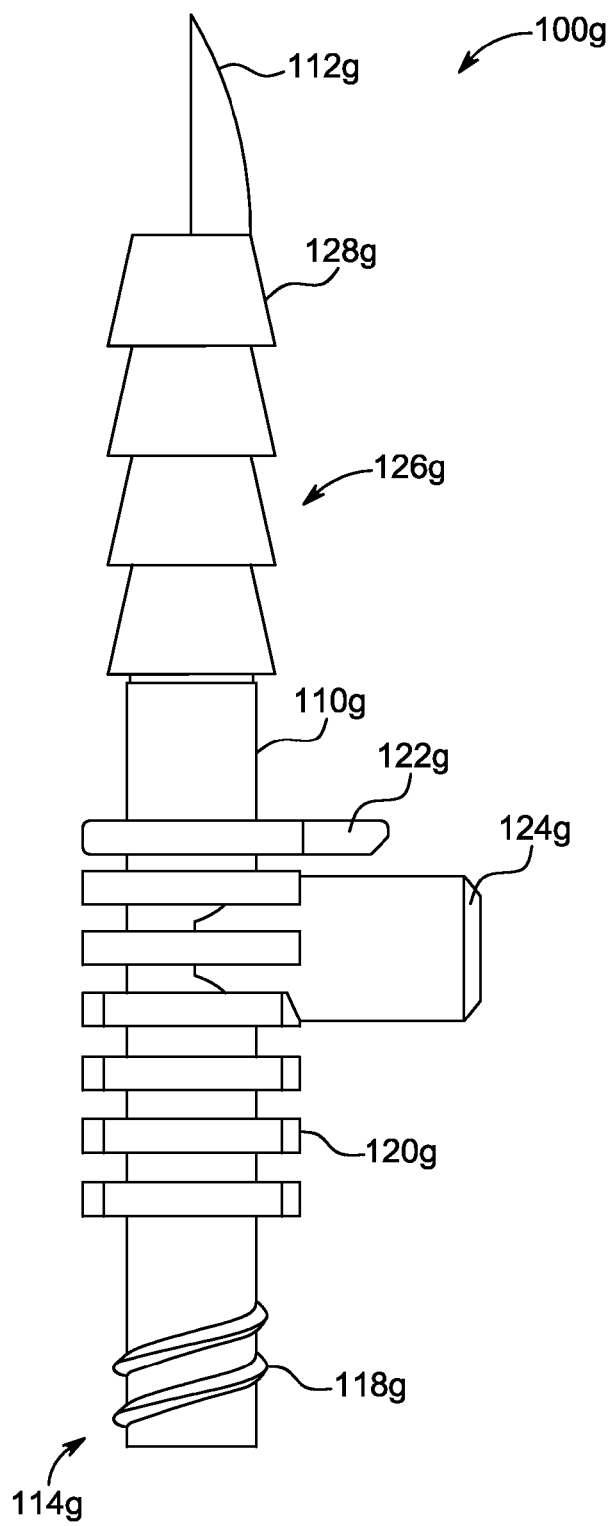
FIG. 8B is a side view of the attachment device shown in FIG. 8A.

Referring to FIGS. 8A-8B, the attachment device 100g is shown in accordance with a seventh embodiment. The attachment device 100g is substantially similar to the attachment device 100f described with reference to FIGS. 7A-7C above. Reference numerals 110g-124g in FIGS. 8A-8B are used to illustrate equivalent components as reference numerals 110f-124f in FIGS. 7A-7C. Whereas the plurality of barbs 128f in FIGS. 7A-7C are separated into groups between the distal and proximal ends, the plurality of barbs 128g in FIGS. 8A-8B extends along the entire length of the body 110g. The barbs 128g are adapted to engage the sidewall of the outlet port 106 of the medical container 102 and to prevent withdrawal of the attachment device 100g after the attachment device 100g is inserted into medical container 102 (shown in FIG. 1).

Figure 9A:
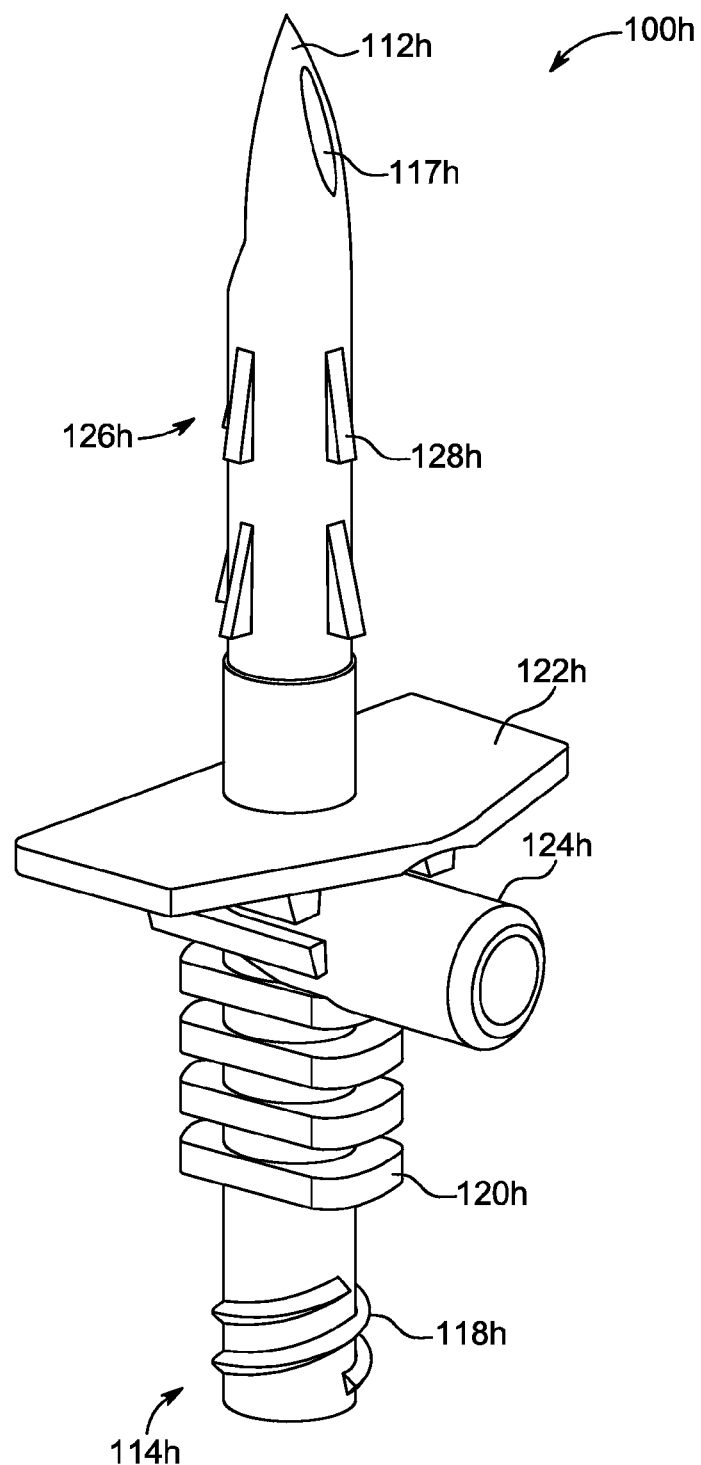
FIG. 9A is a front perspective view of an attachment device for a medical container in accordance with an eighth embodiment.
Figure 9B:
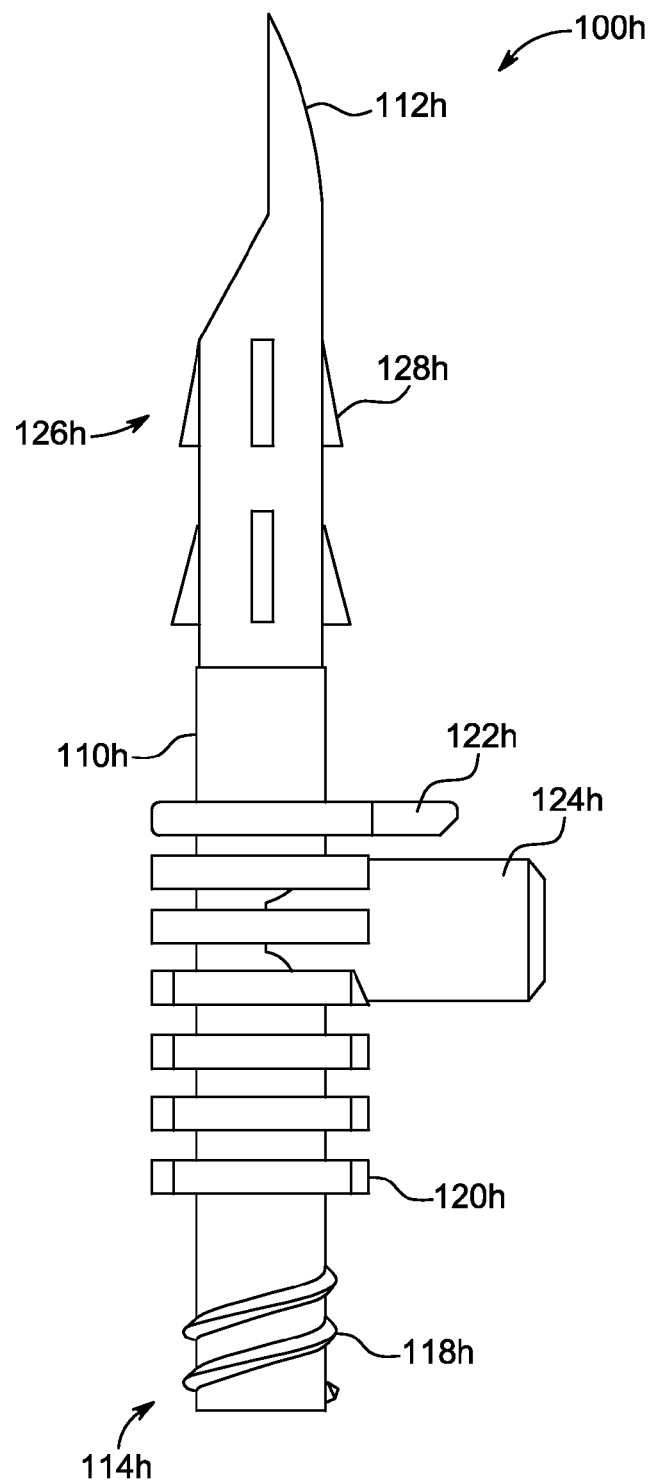
FIG. 9B is a side view of the attachment device shown in FIG. 9A.

Referring to FIGS. 9A-9B, the attachment device 100h is shown in accordance with an eighth embodiment. The attachment device 100h is substantially similar to the attachment device 100a described with reference to FIGS. 2A-2D above. Reference numerals 110h-124h in FIGS. 9A-9B are used to illustrate equivalent components as reference numerals 110a-124a in FIGS. 2A-2D. The attachment device 100h includes at least one retaining element 126h adapted to prevent withdrawal of the attachment device 100h from the outlet port 106 of the medical container 102 (shown in FIG. 1). The at least one retaining element 126h includes a plurality of barbs 128h extending radially outward from the body 110h. Each barb 128h extends around a portion of the circumference of the body 110h. Each barb 128h is angled relative to the longitudinal axis of the attachment device 100h such that each one barb 128h is pointed from the proximal end 114h toward the distal end 112h. The barbs 128h may be arranged in a plurality of rows offset along the longitudinal length of the body 110h. Additionally, the barbs 128h in each row may be spaced apart evenly or non-evenly around the circumference of the body 110h. The barbs 128h from one row may be aligned or offset relative to the barbs 128h in an adjacent row in a direction of the longitudinal length of the body 110h. The barbs 128h are adapted to engage the sidewall of the outlet port 106 of the medical container 102 and to prevent withdrawal of the attachment device 100h after the attachment device 100h is inserted into the medical container 102. Alternatively, or in addition, the barbs 128h are configured to allow insertion of the attachment device 100h through the sealing membrane 108 but prevent withdrawal of the attachment device 100h once inserted through the sealing membrane 108.

Figure 10:
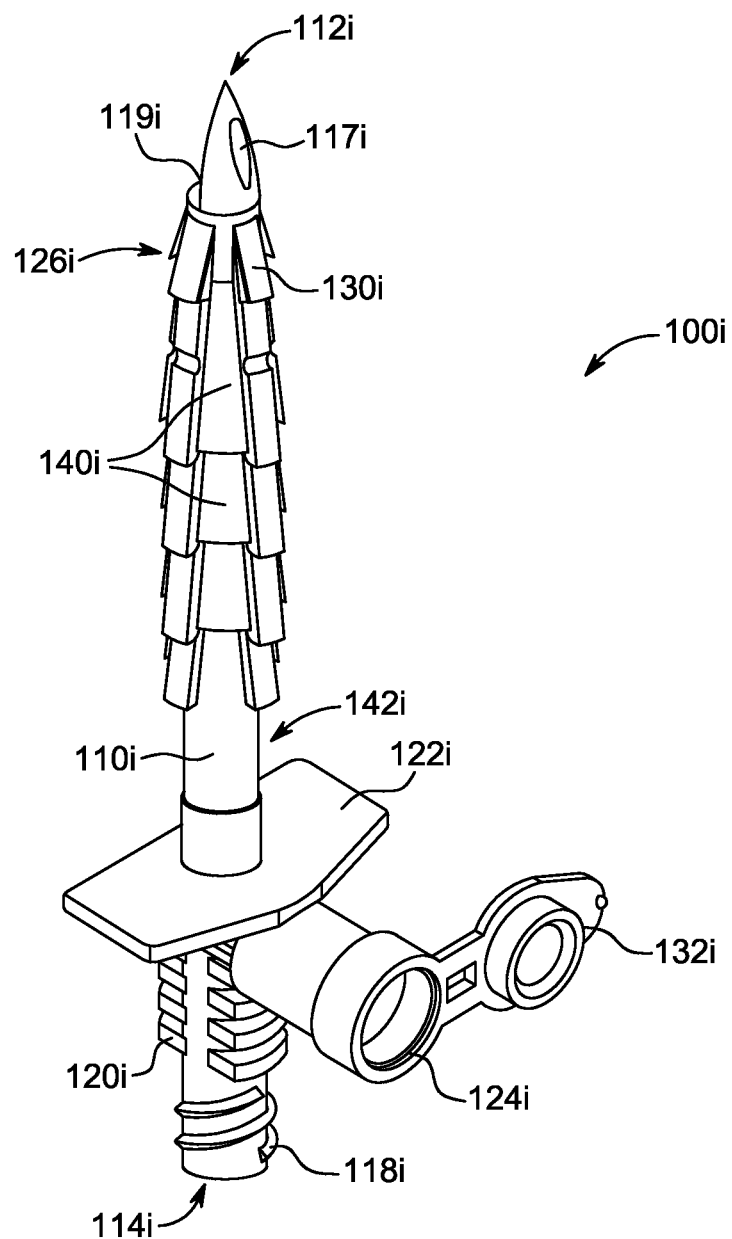
FIG. 10 is a front perspective view of an attachment device for a medical container in accordance with a ninth embodiment.

With reference to FIG. 10, the attachment device 100*i* is shown in accordance with a ninth embodiment. The attachment device 100*i* includes a body 110*i* having a pointed distal end 112*i* configured for puncturing a sealing membrane 108 of a medical container 102 (shown in FIG. 1). The body 110*i* further includes a proximal end 114*i* configured for connecting to a fluid path set 116 (shown in FIG. 1). The body 110*i* is generally hollow with a first fluid channel 117*i* and a second fluid channel 119*i* (also shown in FIG. 12) extending between the distal end 112*i* and the proximal end 114*i*. The first fluid channel 117*i* is configured for delivering the medical fluid between the interior of the medical container 102 and the fluid path set 116. The second fluid channel 119*i* may be an air inlet channel that allows the void created by a departing fluid to be replaced with outside air.

The attachment device 100*i* is removably connectable to the fluid path set 116 using, for example, a Luer-type connector 118*i* provided at the proximal end 114*i*. The Luer-type connector 118*i* on the attachment device 100*i* may be a male or female end configured for removable connection with the corresponding female or male end, respectively, on the fluid path set. One of ordinary skill in the art will understand that the Luer-type connector 118*i* may be replaced with any other known connector for connecting the attachment device 100*i* to the fluid path set 116.

With continuing reference to FIG. 10, the attachment device 100*i* further includes a gripping surface 120*i* having one or more ribs that facilitate handling of the attachment device 100*i* during insertion into the medical container. The gripping surface 120*i* is provided at the proximal end 114*i*. In one embodiment, the gripping surface 120*i* has at least one flattened portion to prevent rotation of the attachment device 100*i* during insertion through the membrane 108 or during connection to the fluid path set 116. The gripping surface 120*i* may be ergonomically shaped to conform to the shape of the user's fingers to facilitate handling of the attachment device 100*i*. A tab 122*i* may be provided distally of the gripping surface 120*i* to prevent accidental contamination of the attachment device 100*i* by contact with a non-sterilized surface. The tab 122*i* extends radially outward and substantially perpendicular to a longitudinal axis of the body 110*i*.

The attachment device 100*i* further includes an auxiliary port 124*i* at the proximal end 114*i*. The auxiliary port 124*i* is adapted for connection to a syringe (not shown) or other fluid transfer device for injecting a second medical fluid into or withdrawing a medical fluid from the medical container 102 through the attachment device 100*i*. The auxiliary port 124*i* connects to the fluid channel 117*i* extending along the longitudinal length of the attachment device 100*i*. The auxiliary port 124*i* may be oriented substantially perpendicular to the fluid channel 117*i* or it may be inclined at an angle relative to the fluid channel 117*i*. In one embodiment, the auxiliary port 124*i* may have a pierceable seal for sealing the auxiliary port 124*i* until the seal is pierced by the fluid transfer device. The attachment device 100*i* may further include a cap element 132*i* for selectively closing the auxiliary port 124*i*.

Figure 11:
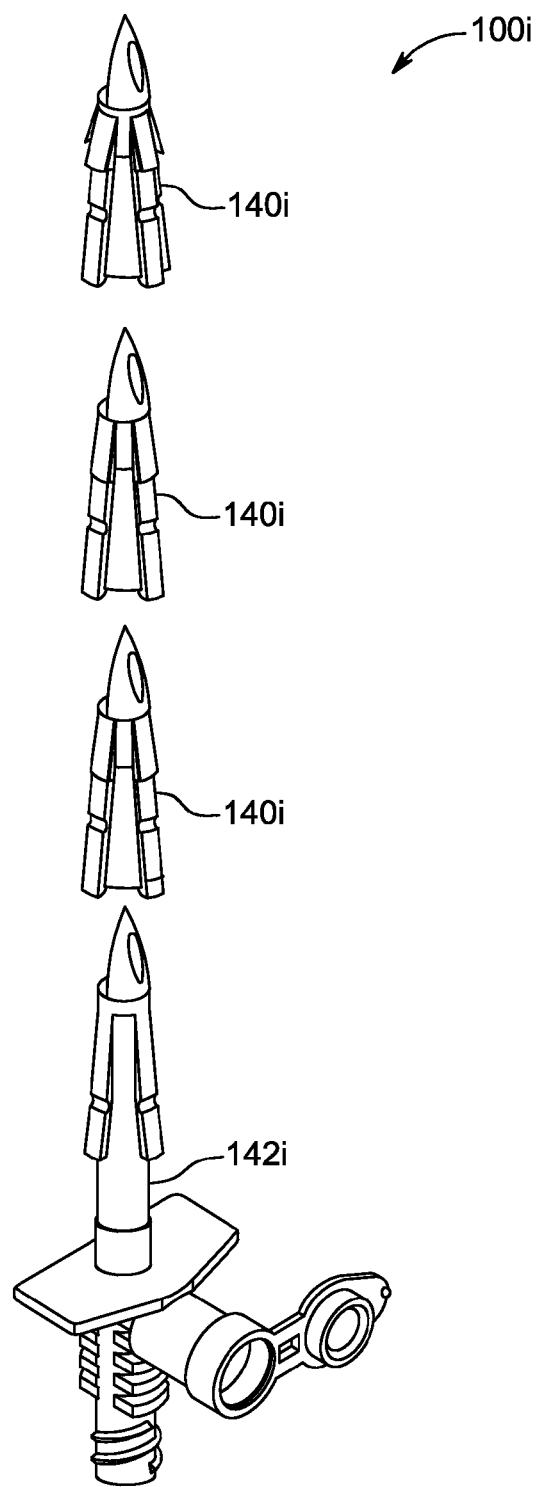
FIG. 11 is an exploded view of the attachment device shown in FIG. 10.

As shown in FIGS. 10-11, the attachment device 100*i* includes one or more removable elements 140*i* in a stackable, nested arrangement on a base element 142*i*. The base element 142*i*, shown in detail in FIG. 13, is substantially similar to the attachment device 100*a* described with reference to FIGS. 2A-2D. A first removable element 140*i* is positioned over the distal end 112*i* of the base element 142*i* and is retained thereon by a locking mechanism 144*i* (shown in FIGS. 12 and 14), as will be described in greater detail hereinafter. One or more additional removable elements 140*i* may be positioned over the distal end 112*i* of the first removable element 140*i* in a stacked, nested arrangement such that the one or more additional removable elements 140*i* cover at least a portion of the first removable element 140*i*.

Figure 12:
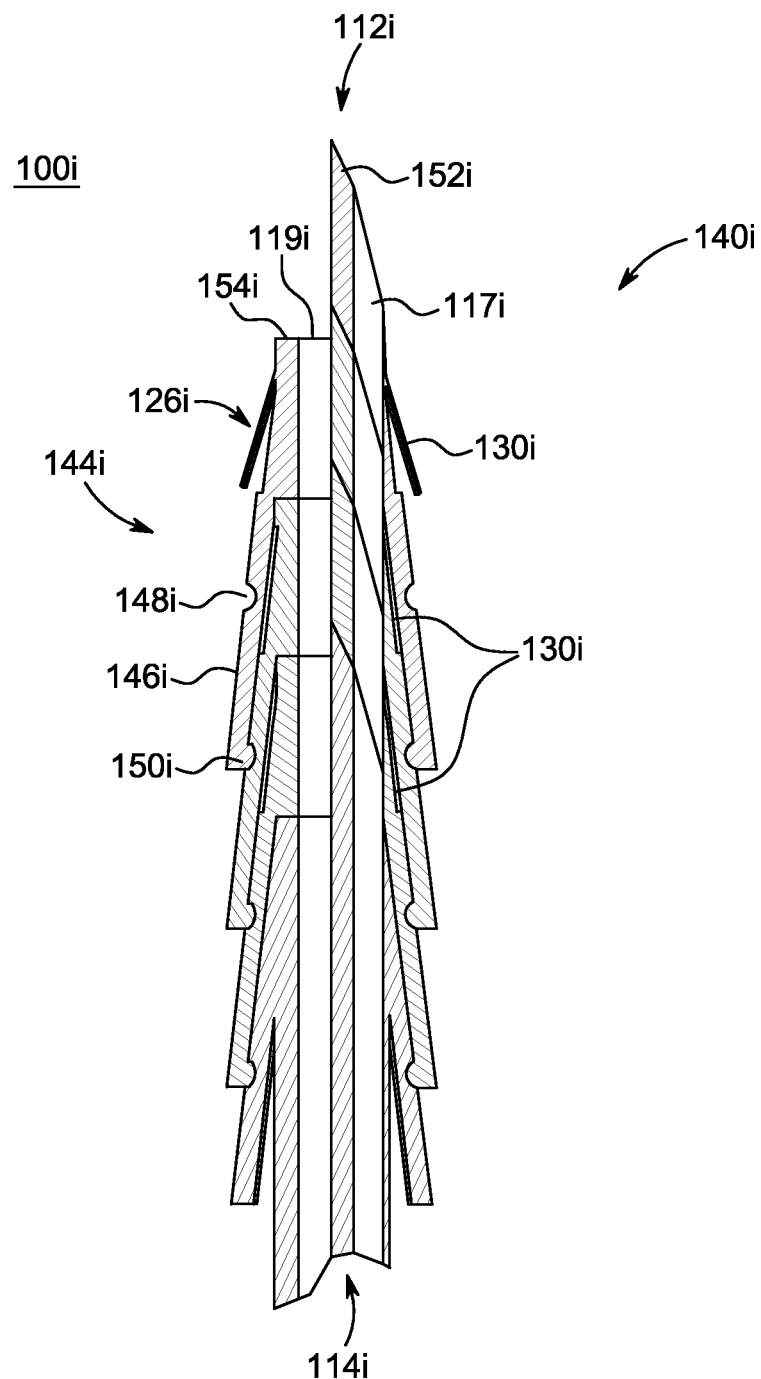
FIG. 12 is a cross-sectional view of a portion of the attachment device shown in FIG. 10.
Figure 13:
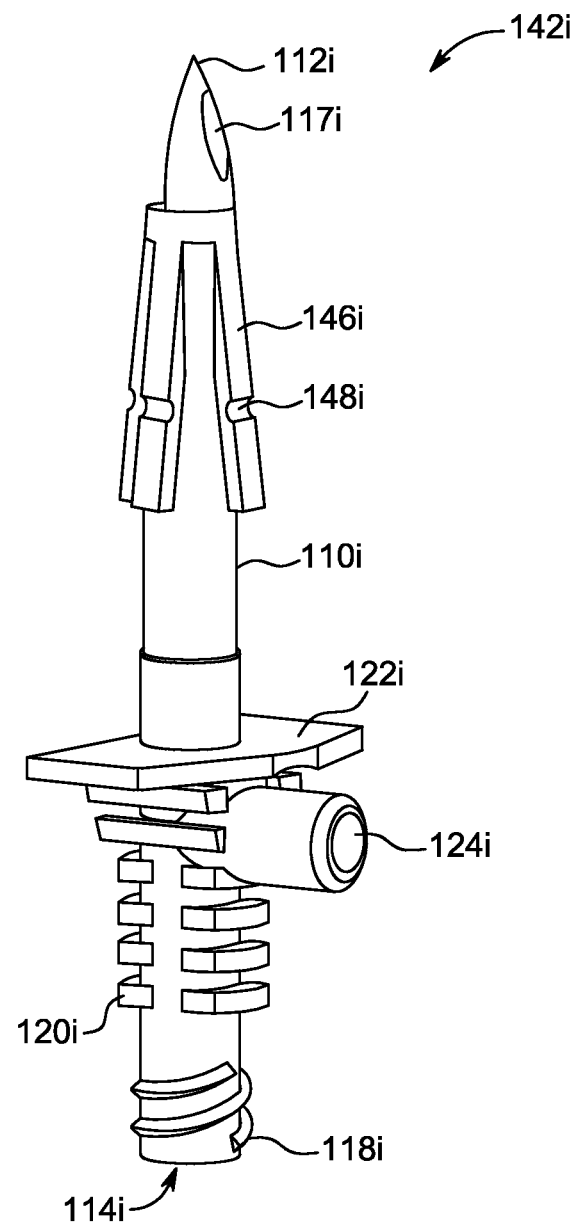
FIG. 13 is a perspective view of a base element of the attachment device shown in FIG. 10.

With reference to FIG. 12, a cross-sectional view of a plurality of stacked removable elements 140*i* is illustrated. The plurality of removable elements 140*i* are desirably nested together in an interlocking arrangement held together by the locking mechanism 144*i* provided between successive removable elements 140*i*. The locking mechanism 144*i* includes at least one barb 146*i* extending radially outward from the body of the removable element 140*i* and the base element 142*i*. The at least one barb 146*i* extends around at least a part of the circumference of the removable element 140*i* and the base element 142*i*. The at least one barb 146*i* is angled relative to the longitudinal axis of the attachment device 100*i* such that the at least one barb 146*i* is pointed from the proximal end 114*i* toward the distal end 112*i*. Each barb 146*i* includes a groove 148*i* that extends radially inward from an outer surface of the barb 146*i* and a tab 150*i* that extends radially inward from an inner surface of the barb 146*i*. Base member 142*i* further includes a groove 148*i* on barb 146*i* (see FIG. 13). The groove 148*i* of one removable element 140*i* or base member 142*i* is configured to receive the tab 150*i* of the removable element 140*i* stacked on top of the other removable element 140*i* or base member 142*i* and lock the removable elements 140*i* such that they cannot be separated without disengaging the tab 150*i* from the groove 148*i*.

With continuing reference to FIGS. 10 and 12, each removable element 140*i* has at least one retaining element 126*i* adapted to prevent withdrawal of the attachment device 100*i* from the outlet port 106 of the medical container 102. The at least one retaining element 126*i* includes at least one deflectable retaining element 130*i*, for example in the form of an expandable tab, provided at the distal end 112*i*. One end of the at least one radially or outwardly deflectable retaining element 130*i* is connected to the body of the removable element 140*i* while the other end of the at least one deflectable retaining element 130*i* is movable relative to the body of the removable element 140*i*. The at least one deflectable retaining element 130*i* is adapted to be deflected or collapsed against the body of a first removable element 140*i* when a second removable element 140*i* is stacked on the first removable element 140*i*. The at least one deflectable retaining element 130*i* is also adapted to expand against the sidewall of the outlet port 106 or expand outside the outlet port 106 when the distal end 112*i* is inserted through the outlet port 106 and into the interior volume of the medical container 102. The at least one deflectable retaining element 130*i* is adapted to prevent withdrawal of the attachment device 100*i* after the attachment device 100*i* is inserted into the medical container 102. In an initial state, such as before being inserted through the membrane 108, the at least one deflectable retaining element 130*i* extends radially outward relative to the longitudinal length of the body of the removable element 140*i*.

After being inserted into the medical container 102, the at least one deflectable retaining element 130*i* at the most distal end of stacked retaining elements deflects in a radially outward direction if the attachment device 100*i* is attempted to be removed from the medical container 102. In this way, the at least one deflectable retaining element 130*i* prevents the removable element 140*i* from being withdrawn from the medical container 102. By pulling the attachment device 100*i* in a direction opposite to the insertion direction, the locking mechanism 144*i* between the most distal removable element 140*i* that is inserted into the medical container 102 and the next adjacent removable element 140*i* or base element 142*i* is disengaged to disconnect the attachment device 100*i* from the most distal removable element 140*i* that is inserted into the medical container. In this manner, the most distal removable element 140*i* is detached from the base element 142*i* and retained within the medical container 102. The locking mechanism 144*i* disengages when the tab 150*i* on the most distal removable element 140*i* that is inserted into the medical container 102 is disconnected from the groove 148*i* on the next adjacent removable element 140*i* or base element 142*i*. In this manner, the disconnected attachment device 100*i* can be reconnected with additional medical containers by inserting the next removable element 140*i* or the base element 142*i* into the container.

Figure 14:
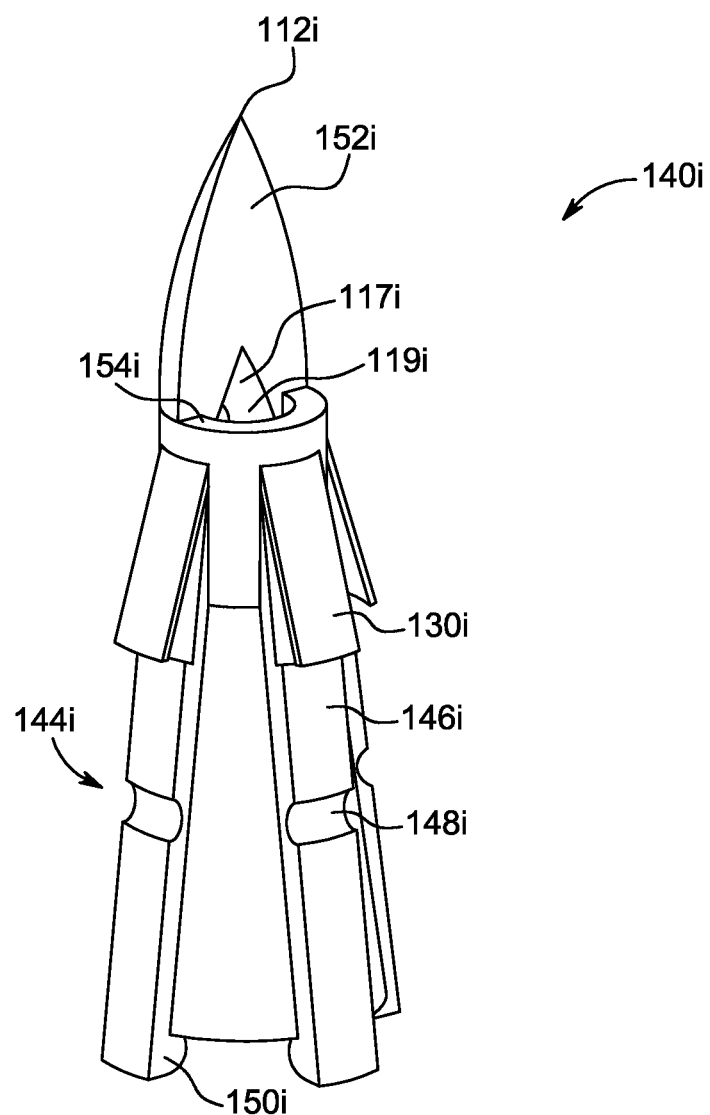
FIG. 14 is a perspective view of a removable element of the attachment device shown in FIG. 10.
Figure 15:
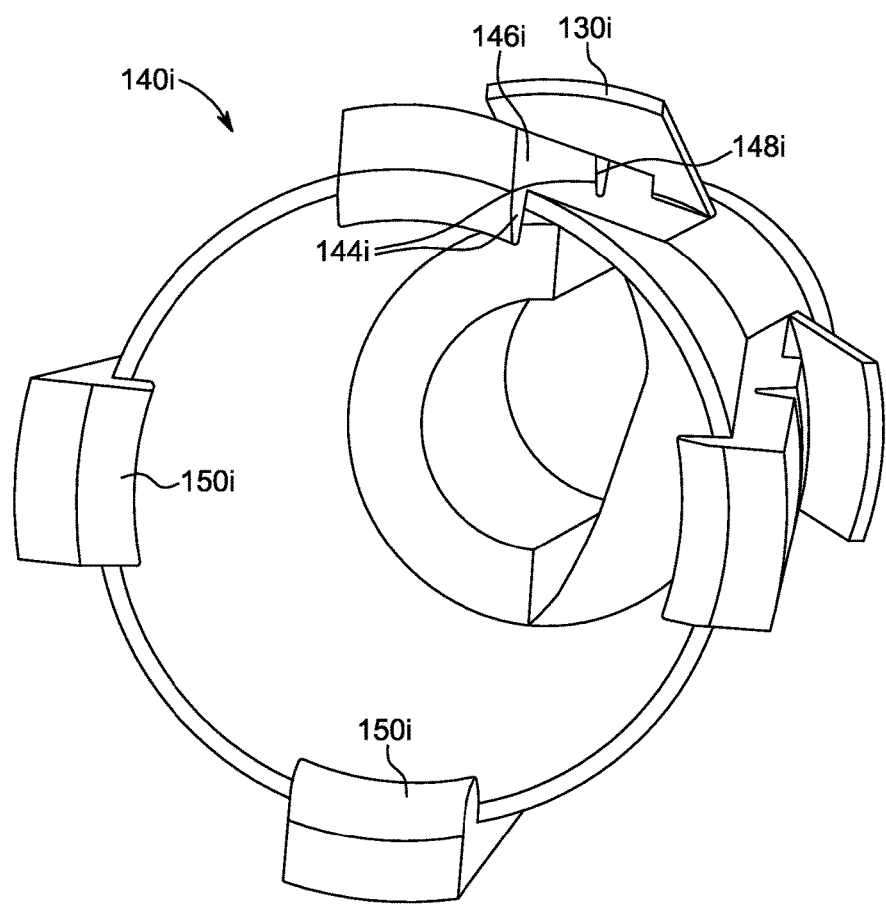
FIG. 15 is a bottom perspective view of the removable element shown in FIG. 14.

As illustrated in FIGS. 12 and 14-15, the distal end of each removable element 140*i* includes a pointed tip 152*i* associated with the first fluid channel 117*i* and a flattened portion 154*i* associated with a second fluid channel 119*i* that is generally parallel to the first fluid channel 117*i*. The second fluid channel 119*i* may be an air inlet channel that allows the void created by a departing fluid to be replaced with outside air. The second fluid channel 119*i* may have an air filter (not shown) to allow air to pass therethrough while preventing the passage of liquid. When stacked together, the removable elements 140*i* are desirably arranged such that the pointed tip 152*i* of one removable element 140*i* is inserted into the pointed tip 152*i* of the adjacent removable element 140*i*. Similarly, the flattened portion 154*i* one removable element 140*i* abuts against the flattened portion 156*i* of the adjacent removable element 140*i*. Arranging the removable elements 140*i* in this manner assures that the first and second fluid channels 117*i*, 119*i* of one removable element 140*i* are aligned with the first and second fluid channels 117*i*, 119*i* of the adjacent removable element 140*i*.

While various embodiments of the attachment device for a medical container were provided in the foregoing description, those skilled in the art may make modifications and alterations to these embodiments without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

The invention claimed is:

1. An attachment device for connecting a fluid path set to a medical container, the attachment device comprising:
   a body having a pointed distal end and a proximal end configured for connecting to the fluid path set;
   one or more removable elements configured to removably connect to the pointed distal end of the body, the one or more removable elements having a distal end configured for extending through a membrane of the medical container;
   at least one fluid channel extending along a longitudinal axis of the body and the one or more removable elements, the at least one fluid channel configured for delivering a medical fluid between the medical container and the fluid path set; and
   at least one retaining element associated with each of the body and each of the one or more removable elements and projecting from the body and each of the one or more removable elements,
   wherein the at least one retaining element on a most distal removable element is configured for non-removably retaining the most distal removable element of the attachment device within the medical container after the attachment device is connected to the medical container, while allowing disengagement and removal of the body and any proximal removable elements.

2. The attachment device of claim 1, wherein the one or more removable elements are stacked in a nested arrangement on the pointed distal end of the body.

3. The attachment device of claim 2, further comprising one or more locking mechanisms, wherein the attachment device comprises a first locking mechanism between the body and a first removable element and separate locking mechanisms between any remaining removable elements.

4. The attachment device of claim 3, wherein the one or more locking mechanisms comprise at least one barb extending radially outward from the body and from each of the one or more removable elements.

5. The attachment device of claim 4, wherein the at least one barb further comprises a groove on an outer surface of the at least one barb or the one or more removable elements and a tab on an inner surface of the at least one barb or the removable elements.

6. The attachment device of claim 5, wherein the groove of the first removable element is configured to receive the tab of a second removable element stacked on top of the first removable element and lock the removable elements such that they cannot be separated without disengaging the tab from the groove.

7. The attachment device of claim 1, wherein the at least one retaining element of the most distal removable element is deflectable toward the body when the most distal removable element is inserted through the membrane of the medical container and wherein the at least one retaining element of the most distal removable element is deflectable away from the body when the attachment device is moved in a direction away from the medical container such that the most distal removable element is detached from the body and retained within the medical container.

8. An attachment device for connecting a fluid path set to a medical container, the attachment device comprising:
   a body having a pointed distal end configured for extending through a membrane of the medical container and a proximal end configured for connecting to the fluid path set;
   at least one fluid channel extending along a longitudinal axis of the body between the distal end and the proximal end, the at least one fluid channel configured for flowing a medical fluid between the medical container and the fluid path set;
   at least one deflectable retaining element extending outward from the body between the pointed distal end and the proximal end; and
   at least one recess provided on the body, wherein the at least one recess is configured for receiving the at least one deflectable retaining element,
   wherein the at least one deflectable retaining element is configured for non-removably retaining the attachment device with the medical container after the attachment device is connected to the medical container.

9. The attachment device of claim 8, wherein the at least one deflectable retaining element has a first end connected to the body and a second end extending radially outward from the body.

10. The attachment device of claim 8, wherein the at least one deflectable retaining element is deflectable toward the body when the attachment device is inserted through the membrane and wherein the deflectable retaining element is deflectable away from the body when the attachment device is moved in a direction away from the medical container.

11. The attachment device of claim 8, further comprising a connector at the proximal end of the body, wherein the connector is configured for connecting to the fluid path set.

12. The attachment device of claim 8, further comprising a gripping surface having one or more ribs extending radially outward from the body at the proximal end of the body.

13. The attachment device of claim 12, further comprising a tab provided distally of the gripping surface, wherein the tab extends radially outward past at least a portion of the gripping surface.

14. The attachment device of claim 8, further comprising an auxiliary port extending through the body, wherein the auxiliary port is in fluid connection with the at least one fluid channel.

15. The attachment device of claim 14, wherein the auxiliary port has a removable cap element configured for enclosing the auxiliary port.

16. The attachment device of claim 8, further comprising at least one barb extending radially outward from the body and circumscribing a circumference of the body, wherein the at least one barb is angled relative to the longitudinal axis of the body such that the at least one barb is pointed from the proximal end toward the pointed distal end.

17. An attachment device for connecting a fluid path set to a medical container, the attachment device comprising:
  a body having a pointed distal end configured for extending through a membrane of the medical container and a proximal end configured for connecting to the fluid path set;
  at least one fluid channel extending along a longitudinal axis of the body between the distal end and the proximal end, the at least one fluid channel configured for flowing a medical fluid between the medical container and the fluid path set;
  at least one deflectable retaining element extending outward from the body between the pointed distal end and the proximal end;
  at least one recess provided on the body, wherein the at least one recess is configured for receiving the at least one deflectable retaining element; and
  at least one barb extending radially outward from the body and circumscribing a circumference of the body,
  wherein the at least one deflectable retaining element and the at least one barb are configured for non-removably retaining the attachment device with the medical container after the attachment device is connected to the medical container.

18. The attachment device of claim 17, wherein the at least one deflectable retaining element is deflectable toward the body when the attachment device is inserted through the membrane and wherein the at least one deflectable retaining element is deflectable away from the body when the attachment device is moved in a direction away from the medical container.

19. The attachment device of claim 17, wherein the at least one barb is angled relative to the longitudinal axis of the body such that the at least one barb is pointed from the proximal end toward the pointed distal end.

\* \* \* \* \*